United States Patent
Hashimoto et al.

(10) Patent No.: US 6,277,503 B1
(45) Date of Patent: Aug. 21, 2001

(54) ORGANIC ELECTROLUMINESCENT COMPONENT

(75) Inventors: Mitsuru Hashimoto; Mutsumi Suzuki, both of Yokohama; Masao Fukuyama, Tokyo, all of (JP)

(73) Assignee: Matsushita Electric Idustrial Co., LTD, Osaka (JP)

( * ) Notice: Subject to any disclaimer, the term of this patent is extended or adjusted under 35 U.S.C. 154(b) by 0 days.

(21) Appl. No.: 09/260,066

(22) Filed: Mar. 2, 1999

(30) Foreign Application Priority Data

Mar. 3, 1998 (JP) .................................................. 10-76819

(51) Int. Cl.$^7$ .............................. B32B 19/00; B32B 9/00
(52) U.S. Cl. ............................................. 428/690; 428/917
(58) Field of Search ..................................... 428/690, 917

(56) References Cited

FOREIGN PATENT DOCUMENTS 63-264629   11/1988   (JP) .
2554771    8/1996   (JP) .

OTHER PUBLICATIONS

126:124569 "Organic Electroluminescent Device" Inomoto et al 1996.*
126: 81993 "Organic Electroluminescent Device Having Examine Hole–Injecting Transporting Layer" Inomoto et al 1996.*
125: 179869 "Towards . . . Phenomena" "Corril et al." 1996.*
124: 302024 "Electroluminescent Devices" Suzuki 1995.*
124: 70429 "High Efficient . . . New Dopant" Hirokawa et al 1995.*
123: 270301 "Organic Thin Film Light Emitting Device" Sugata et al. 1995.*
123: 155457 "Organic Electroluminescent . . . Derivatives" Nohara et al. 1994.*
123: 213432 "Organic Thin Film Electroluminescent Devices" Ookura et al. 1995.*
123: 43976 "Organic . . . Layer" Sugata et al 1995.*
122: 302602 "Organic . . . Layer" Ookura et al. 1995.*
122: 278269 "Organic Electroluminescent Element" Inokida 1994.*
122: 200809 "Thin Film . . . Layer" Karoda et al 1995.*
122: 251699 "Organic Electroluminescent Devices" Inokida 1995.*
122: 67929 "Electroluminescent Device" Takahashi 1994.*
122: 200677 "Multicolor . . . Devices" Takeuchi 1994.*
121: 241365 "Charge—Injection . . . the Same" Hotokawa et al. 1994.*
120: 334569 "Organic . . . Layer" Suzuki et al. 1994.*
120: 204101 "Electroluminescent Device" Takabashi et al. 1993.*
120: 177613 "Organic Electroluminescent Elements" Hoto-Kawa et al. 1993.*
119: 259214 "Organic Electroluminescent Device" Hotokawa et al. 1993.*
119: 17675 "Dispersion Type Electroluminescent Devices" Mori et al. 1992.*
119: 17620 "Organic . . . Elements" Higashi et al. 1992.*
117: 260796 "Studies . . . Cells" Higashi et al. 1992.*
117: 131228 "Preparation . . . Derivatives" Hasegawa et al. 1992.*

(List continued on next page.)

Primary Examiner—Duc Truong
(74) Attorney, Agent, or Firm—Israel Gopstein

(57) ABSTRACT

The present invention provides an organic electroluminescent component in which use is made of the particular aromatic methylidene compound represented by the general formula (1). The component of the invention has the ability of high brightness luminescence with stability in low voltage application.

4 Claims, 2 Drawing Sheets

OTHER PUBLICATIONS

117: 121752 "Organic Electroluminescent Devices" Mori et al. 1992.*

114: 153731 "Electroluminescent Devices" Hotokawa et al. 1990.*

111: 123970 "Electroluminescent . . . Zone" Tang et al. 1988.*

102: 14796 "Organic . . . Efficiencies" Van Slyke 1984.*

"Organic electroluminescent diodes" by C.W. Tang et al; Appl. Phys. Lett. 51(12), Sep. 21, 1987; pp. 913–915.

* cited by examiner

ORGANIC ELECTROLUMINESCENT COMPONENT

BACKGROUND OF THE INVENTION (i) Field of the Invention

The present invention relates to an organic electroluminescent component, specifically an organic electroluminescent component using a particular aromatic methylidene compound which has the ability of high brightness luminescence in low voltage application with excellent stability.

(ii) Description of the Related Art

An electroluminescent component which uses an electroluminescent phenomenon of substances is self-luminescence type unlike a liquid crystal component. Accordingly, its visibility is high and, therefore, it is possible to obtain clear indication when used for displays. Because it is a complete solid state component, it has the characteristics such as excellent impact resistance. In future, the electroluminescent component is expected to find use widely for a back light of thin type displays or liquid crystal displays or plane light sources.

One of electroluminescent components which are now put into practical use is a dispensing type electroluminescent component in which inorganic materials such as zinc sulfide are used. However, these dispersing type electroluminescent components need comparatively high a.c. voltage for their drive and, therefore, have problems such as complicates driving circuits or low brightness. Now, these are not widely put into practical use.

Meanwhile, organic electroluminescent components using organic materials have been spotlighted since C. W. Tang et al. proposed a component having a laminate structure in which an electron-transporting organic fluorescent substance and a positive hole-transporting organic substance are stacked and both carriers for electrons and for positive holes are injected into the fluorescent substance layer to generate luminescence in 1987 [C. W. Tang and S. V. VAN Slyke, Appl. Phys. Lett., Vol. 51, p. 913–915 (1987); Japanese Patent Application Laid-Open No. Sho-63-264629]. It is described that luminescence of at least 1000 cd/m² may be obtained under a driving voltage of not more than 10 V in these components. Various investigations for these materials have been carried out actively since the aforementioned proposal. As a result, various materials and component structures are now proposed and researches for their practical use are performed actively.

On the other hand, in fact, organic electroluminescent components using the organic materials proposed still have various problems. Examples of these problems include the following phenomena. Functions of the components deteriorate to lower luminescence brightness in a driving state or even in a non-driving state, i.e. during storing. Alternatively, in a driving or non-driving state, there happens the deterioration that non-luminescent regions called dark spot appear and grow up, which, finally, lead to a short circuit in the components that causes ruptures. These phenomena are considered to be essential problems in the materials used there. In the present state, it is hardly recognized that the components have sufficient lives for their practical use. Therefore, their practical use is restricted to devices in which a comparatively short life may be accepted.

Alternatively, mention is made of another problem that, in the case where the components are colored, systems or materials therefor are not sufficiently prepared. In order to solve these problems and to attain their wide practical use, it is an important technical object to research for new high functional luminescent materials and electric charge transporting materials.

SUMMARY OF THE INVENTION

The present invention has been effected in such a state of the organic electroluminescent components. After the earnest researches for organic electroluminescent components which are able to generate high brightness luminescence under low voltages, the present inventors have now found that particular organic compounds are excellent as a material for the organic electroluminescent components. This leads to the invention.

That is, the present invention provides an organic electroluminescent component, characterized in that use is made of a particular aromatic methylidene compound represented by the following general formula:

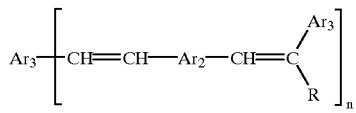

(formula 2)

wherein $Ar_1$ stands for a substituted or unsubstituted aromatic hydrocarbon residue having 2 to 6 valences or a substituted or unsubstituted aromatic heterocyclic hydrocarbon residue having 2 to 6 valences; $Ar_2$ stands for a divalent substituted or unsubstituted aromatic hydrocarbon residue or a divalent substituted or unsubstituted aromatic heterocyclic hydrocarbon residue; $Ar_3$ stands for a substituted or unsubstituted aromatic hydrocarbon residue or a substituted or unsubstituted aromatic heterocyclic hydrocarbon residue; R stands for a substituted or unsubstituted aromatic hydrocarbon residue or a substituted, unsubstituted aromatic heterocyclic hydrocarbon residue, a substituted or unsubstituted alkyl group or hydrogen atom (excluding the case where $Ar_3$ is a phenyl group), $Ar_3$ and R being able to form a ring together with each other; and n stands for a positive number of 1 to 6.

BRIEF DESCRIPTION OF THE DRAWINGS

In FIGS. 1 to 4, symbols have the following meanings, respectively: (1) cathode; (2) positive hole-transporting layer; (3) luminescent layer; (4) electron-transporting layer; and (5) anode.

DETAILED DESCRIPTION OF THE INVENTION

Figure 1:
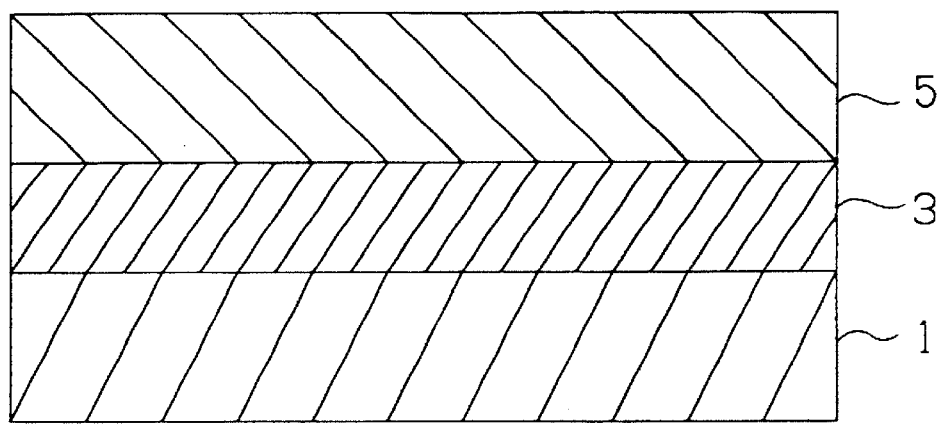
FIG. 1 is a schematic sectional view of a component consisting of a cathode, a luminescent layer and an anode, which is one embodiment of the present invention.

Next, $Ar_1$, $Ar_2$, $Ar_3$ and R in the aforesaid general formula will be described more specifically.

In Ar$_1$, as an example of the substituted or unsubstituted aromatic hydrocarbon residue having 2 to 6 valences and the substituted or unsubstituted aromatic heterocyclic hydrocarbon residue having 2 to 6 valences, mention is made of the residues of the following compounds: substituted or unsubstituted benzene having 2 to 5 valences, hexavalent benzene, substituted or unsubstituted biphenyl having 2 to 6 valences, substituted or unsubstituted terphenyl having 2 to 6 valences, substituted or unsubstituted quarterphenyl having 2 to 6 valences, substituted or unsubstituted quinquephenyl having 2 to 6 valences, substituted or unsubstituted naphthalene having 2 to 6 valences, substituted or unsubstituted acenaphtene having 2 to 6 valences, substituted or unsubstituted acenaphthylene having 2 to 6 valences, substituted or unsubstituted anthracene having 2 to 6 valences, substituted or unsubstituted phenanthrene having 2 to 6 valences, substituted or unsubstituted pyrene having 2 to 6 valences, substituted or unsubstituted fluorene having 2 to 6 valences, substituted or unsubstituted fluorenone having 2 to 6 valences, substituted or unsubstituted anthraquinone having 2 to 6 valences, substituted or unsubstituted phenanthrenequinone having 2 to 6 valences, substituted or unsubstituted binaphthyl having 2 to 6 valences, substituted or unsubstituted triphenylbenzene having 2 to 6 valences, substituted or unsubstituted thiophene having 2 to 6 valences, substituted or unsubstituted pyrrole having 2 to 4 valences, substituted or unsubstituted furan having 2 to 4 valences, substituted or unsubstituted bithiophene having 2 to 6 valences, substituted or unsubstituted pyridine having 2 to 5 valences, substituted or unsubstituted pyridazine having 2 to 4 valences, substituted or unsubstituted pyrimidine having 2 to 4 valences, substituted or unsubstituted pyrazine having 2 to 4 valences, substituted or unsubstituted triazine having 2 to 3 valences, substituted or unsubstituted quinoline having 2 to 6 valences, substituted or unsubstituted isoquinoline having 2 to 6 valences, substituted or unsubstituted cinnoline having 2 to 6 valences, substituted or unsubstituted quinoxaline having 2 to 6 valences, substituted or unsubstituted phthalazine having 2 to 6 valences, substituted or unsubstituted dibenzothiophene having 2 to 6 valences, substituted or unsubstituted dibenzofuran having 2 to 6 valences, substituted or unsubstituted carbazole having 2 to 6 valences, substituted or unsubstituted diphenyloxadiazole having 2 to 6 valences, substituted or unsubstituted diphenylthiophene having 2 to 6 valences, substituted or unsubstituted dithienylbenzene having 2 to 6 valences, etc. Examples of the substituent in Ar$_1$ include a linear or branched alkyl group having 1–12 carbon atoms, a cycloalkyl group such as cyclopentyl or cyclohexyl group, a linear or branched alkoxy group having 1–12 carbon atoms, a halogen atom such as fluorine, chlorine or bromine, cyano group, nitro group, an acyl group such as acetyl or benzoyl group, a carboxyl group and esters thereof, and a substituted alkyl group such as trifluoromethyl or benzyl group. The number of the substituent may be singular or plural. When it is plural, these substituents may be identical to or different from each other.

In Ar$_2$, as an example of the divalent substituted or unsubstituted aromatic hydrocarbon residue and the divalent substituted or unsubstituted aromatic heterocyclic hydrocarbon residue, mention is made of the residues of the following compounds: divalent substituted or unsubstituted benzene, divalent substituted or unsubstituted biphenyl, divalent substituted or unsubstituted terphenyl, divalent substituted or unsubstituted quaterphenyl, divalent substituted or unsubstituted quinquephenyl, divalent substituted or unsubstituted naphthalene, divalent substituted or unsubstituted acenaphtene, divalent substituted or unsubstituted acenaphthylene, divalent substituted or unsubstituted anthracene, divalent substituted or unsubstituted phenanthrene, divalent substituted or unsubstituted pyrene, divalent substituted or unsubstituted fluorene, divalent substituted or unsubstituted fluorenone, divalent substituted or unsubstituted anthraquinone, divalent substituted or unsubstituted phenanthrenequinone, divalent substituted or unsubstituted binaphthyl, divalent substituted or unsubstituted triphenylbenzene, divalent substituted or unsubstituted thiophene, divalent substituted or unsubstituted pyrrole, divalent substituted or unsubstituted furan, divalent substituted or unsubstituted bithiophene, divalent substituted or unsubstituted pyridine, divalent substituted or unsubstituted pyridazine, divalent substituted or unsubstituted pyrimidine, divalent substituted or unsubstituted pyrazine, divalent substituted or unsubstituted triazine, divalent substituted or unsubstituted quinoline, divalent substituted or unsubstituted isoquinoline, divalent substituted or unsubstituted cinnoline, divalent substituted or unsubstituted quinoxaline, divalent substituted or unsubstituted phthalazine, divalent substituted or unsubstituted dibenzothiophene, divalent substituted or unsubstituted dibenzofuran, divalent substituted or unsubstituted carbazole, divalent substituted or unsubstituted diphenyloxadiazole, divalent substituted or unsubstituted diphenylthiophene, divalent substituted or unsubstituted dithienylbenzene, etc. Examples of the substituent in Ar$_2$ include a linear or branched alkyl group having 1–12 carbon atoms, a cycloalkyl group such as cyclopentyl or cyclohexyl group, a linear or branched alkoxy group having 1–12 carbon atoms, a halogen atom such as fluorine, chlorine or bromine, cyano group, nitro group, an acyl group such as acetyl or benzoyl group, carboxyl group and esters thereof, and a substituted alkyl group such as trifluoromethyl or benzyl group. The number of the substituent may be singular or plural. When it is plural, these substituents may be identical to or different from each other.

In Ar$_3$, as an example of the substituted or unsubstituted aromatic hydrocarbon residue and the substituted or unsubstituted aromatic heterocyclic hydrocarbon residue, mention is made of the residues of the following compounds: univalent substituted or unsubstituted benzene, univalent substituted or unsubstituted biphenyl, univalent substituted or unsubstituted terphenyl, univalent substituted or unsubstituted quaterphenyl, univalent substituted or unsubstituted quinquephenyl, univalent substituted or unsubstituted naphthalene, univalent substituted or unsubstituted acenaphtene, univalent substituted or unsubstituted acenaphthylene, univalent substituted or unsubstituted anthracene, univalent substituted or unsubstituted phenanthrene, univalent substituted or unsubstituted pyrene, univalent substituted or unsubstituted fluorene, univalent substituted or unsubstituted fluorenone, univalent substituted or unsubstituted anthraquinone, univalent substituted or unsubstituted phenanthrenequinone, univalent substituted or unsubstituted binaphthyl, univalent substituted or unsubstituted triphenylbenzene, univalent substituted or unsubstituted thiophene, univalent substituted or unsubstituted pyrrole, univalent substituted or unsubstituted furan, univalent substituted or unsubstituted bithiophene, univalent substituted or unsubstituted pyridine, univalent substituted or unsubstituted pyridazine, univalent substituted or unsubstituted pyrimidine, univalent substituted or unsubstituted pyrazine, univalent substituted or unsubstituted triazine, univalent substituted or unsubstituted quinoline, univalent substituted or unsubstituted isoquinoline, univalent substituted or unsubstituted cinnoline, univalent substituted or unsubstituted quinoxaline, univalent substituted or unsubstituted phthalazine, univalent substituted or unsubstituted dibenzothiophene, univalent substituted or unsubstituted dibenzofuran, univalent substituted or unsubstituted carbazole, univalent substituted or unsubstituted diphenyloxadiazole, univalent substituted or unsubstituted diphenylthiophene, univalent substituted or unsubstituted dithienylbenzene, etc. Examples of the substituent in $Ar_3$ include a linear or branched alkyl group having 1–12 carbon atoms, a cycloalkyl group such as cyclopentyl or cyclohexyl group, a linear or branched alkoxy group having 1–12 carbon atoms, a halogen atom such as fluorine, chlorine or bromine, cyano group, nitro group, an acyl group such as acetyl or benzoyl group, carboxyl group and esters thereof, and a substituted alkyl group such as trifluoromethyl or benzyl group. The number of the substituent may be singular or plural. When it is plural, these substituents may be identical to or different from each other.

In R, as an example of the substituted or unsubstituted aromatic hydrocarbon residue, the substituted or unsubstituted aromatic heterocyclic hydrocarbon residue and the substituted or unsubstituted alkyl group, mention is made of the residues of the following compounds: univalent substituted or unsubstituted benzene, univalent substituted or unsubstituted biphenyl, univalent substituted or unsubstituted terphenyl, univalent substituted or unsubstituted quaterphenyl, univalent substituted or unsubstituted quinquephenyl, univalent substituted or unsubstituted naphthalene, univalent substituted or unsubstituted acenaphtene, univalent substituted or unsubstituted acenaphthylene, univalent substituted or unsubstituted anthracene, univalent substituted or unsubstituted phenanthrene, univalent substituted or unsubstituted pyrene, univalent substituted or unsubstituted fluorene, univalent substituted or unsubstituted fluorenone, univalent substituted or unsubstituted anthraquinone, univalent substituted or unsubstituted phenanthrenequinone, univalent substituted or unsubstituted binaphthyl, univalent substituted or unsubstituted triphenylbenzene, univalent substituted or unsubstituted thiophene, univalent substituted or unsubstituted pyrrole, univalent substituted or unsubstituted furan, univalent substituted or unsubstituted bithiophene, univalent substituted or unsubstituted pyridine, univalent substituted or unsubstituted pyridazine, univalent substituted or unsubstituted pyrimidine, univalent substituted or unsubstituted pyrazine, univalent substituted or unsubstituted triazine, univalent substituted or unsubstituted quinoline, univalent substituted or unsubstituted isoquinoline, univalent substituted or unsubstituted cinnoline, univalent substituted or unsubstituted quinoxaline, univalent substituted or unsubstituted phthalazine, univalent substituted or unsubstituted dibenzothiophene, univalent substituted or unsubstituted dibenzofuran, univalent substituted or unsubstituted carbazole, univalent substituted or unsubstituted diphenyloxadiazole, univalent substituted or unsubstituted diphenylthiophene, univalent substituted or unsubstituted dithienylbenzene, methyl group, ethyl group, n-propyl group, isopropyl group, n-butyl group, isobutyl group, sec-butyl group, tert-butyl group, benzyl group, phenethyl group, etc. In R, examples of the substituent in the substituted aromatic hydrocarbon or substituted aromatic heterocyclic hydrocarbon residue include a linear or branched alkyl group having 1–12 carbon atoms, a cycloalkyl group such as cyclopentyl or cyclohexyl group, a linear or branched alkoxy group having 1–12 carbon atoms, a halogen atom such as fluorine, chlorine or bromine, cyano group, nitro group, an acyl group such as acetyl or benzoyl group, carboxyl group and esters thereof, and a substituted alkyl group such as trifluoromethyl or benzyl group. The number of the substituent may be singular or plural. When it is plural, these substituent may be identical to or different from each other.

The aromatic methylidene compound according to the invention may be synthesized by, for example, reacting a corresponding aldehyde derivative with a dialkyl methylphosphonate derivative substituted with aromatic hydrocarbons or aromatic heterocyclic hydrocarbons under basic conditions. Alternatively, it may be synthesized according to another general synthetic methods for stilbene derivatives.

Although the so-called cis- or trans-structural isomer is sometimes present in the aromatic methylidene compound according to the invention, the compound is not restricted to one of the isomers and both isomers can be preferably used in the present invention.

Examples of the present compound will be mentioned below. However, the present compound is not restricted to these compounds.

(formula 3)

(Compound No. 1)

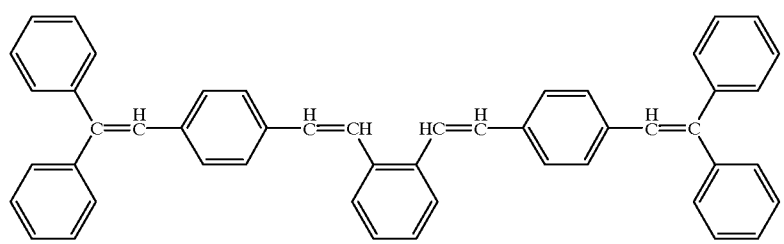

(Compound No. 2)
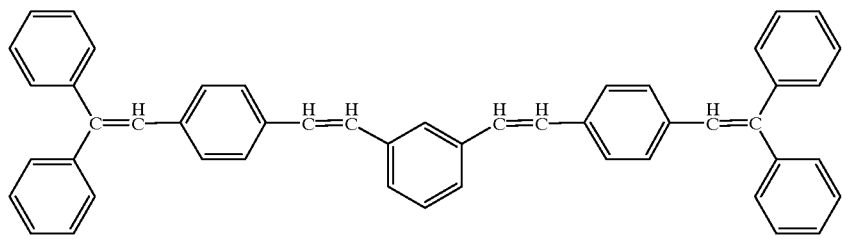
(Compound No. 3)
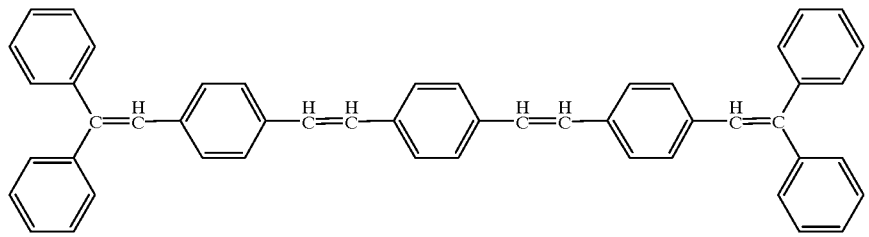
(Compound No. 4)
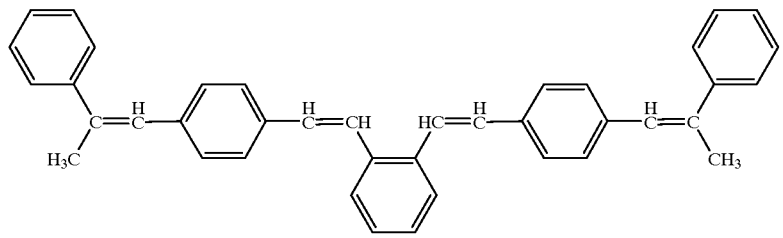
(Compound No. 5)
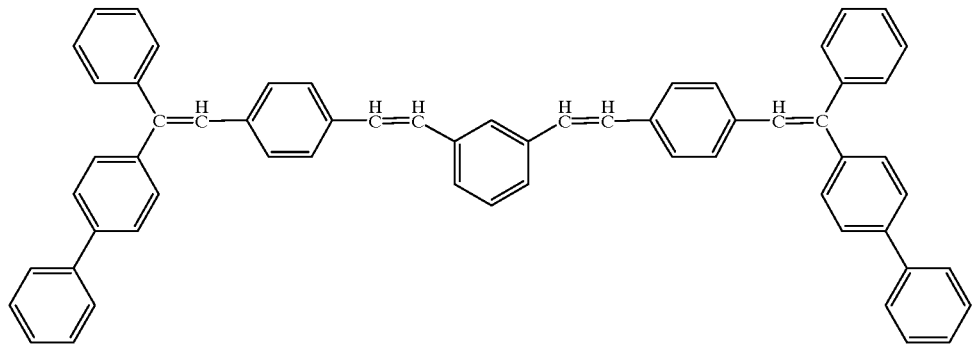
(formula 4)
(Compound No. 6)
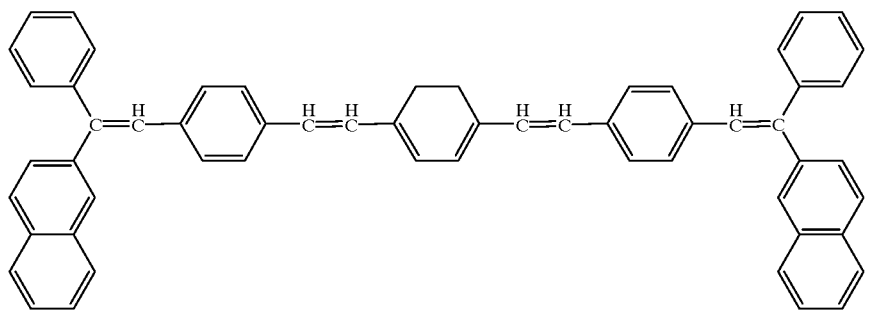

-continued
(Compound No. 7)
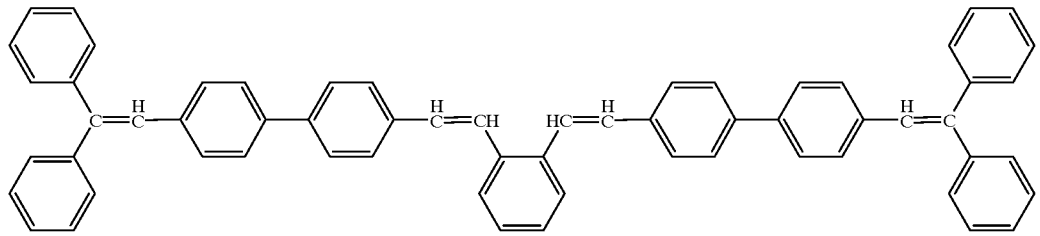
(Compound No. 8)
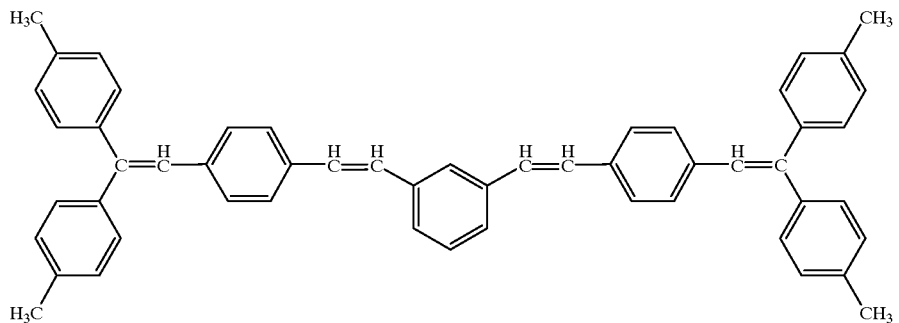
(Compound No. 9)
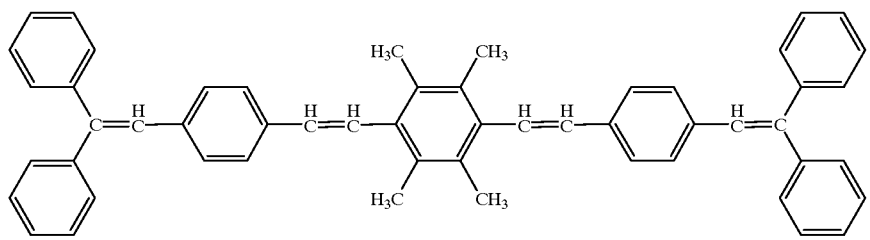
(Compound No. 10)
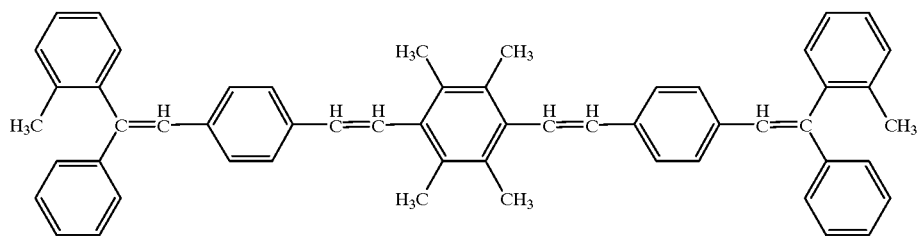
(formula 5)
(Compound No. 11)
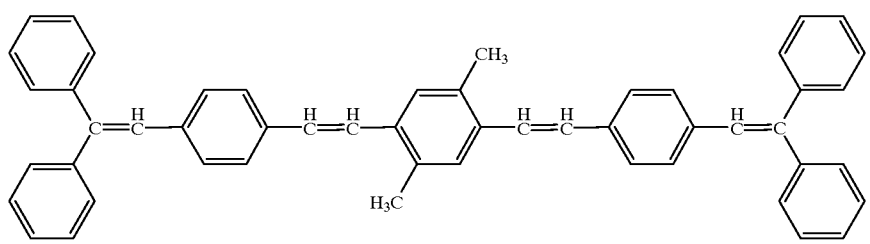

-continued
(Compound No. 12)
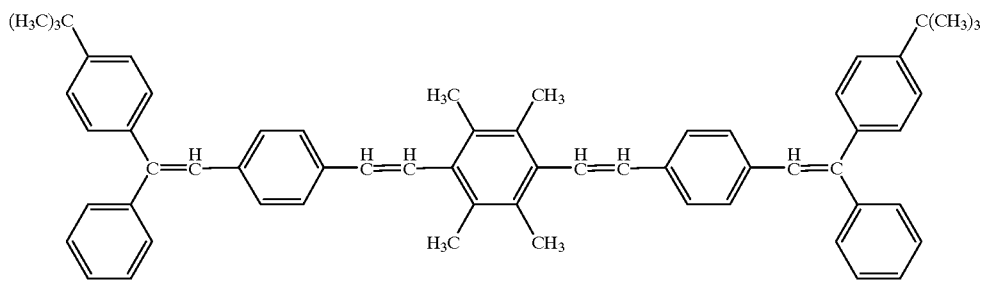
(Compound No. 13)
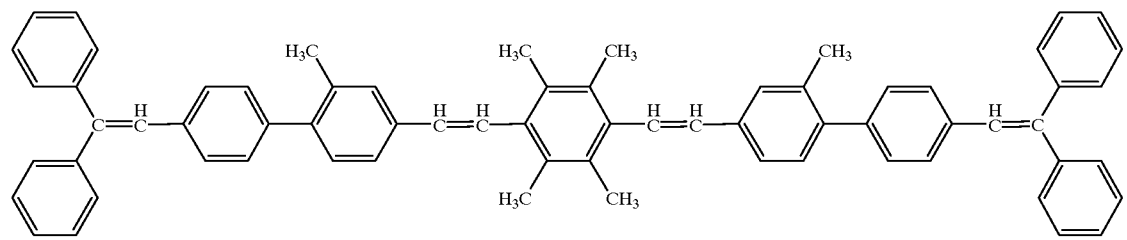
(Compound No. 14)
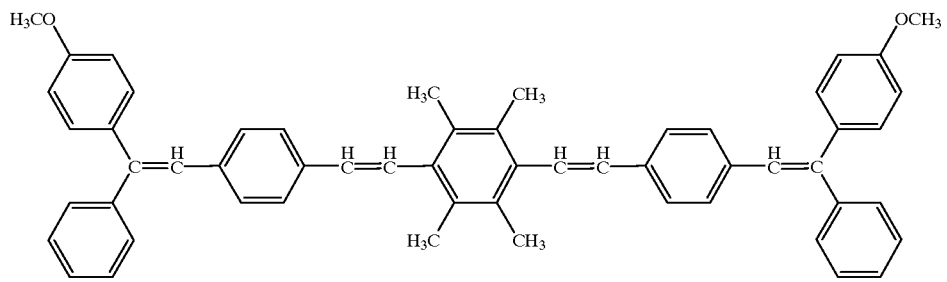
(Compound No. 15)
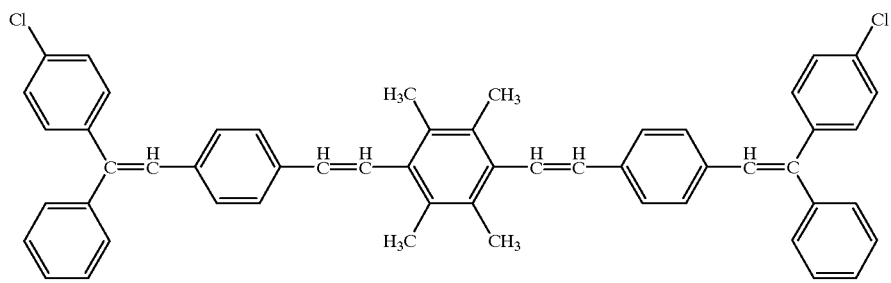
(formula 6)
(Compound No. 16)
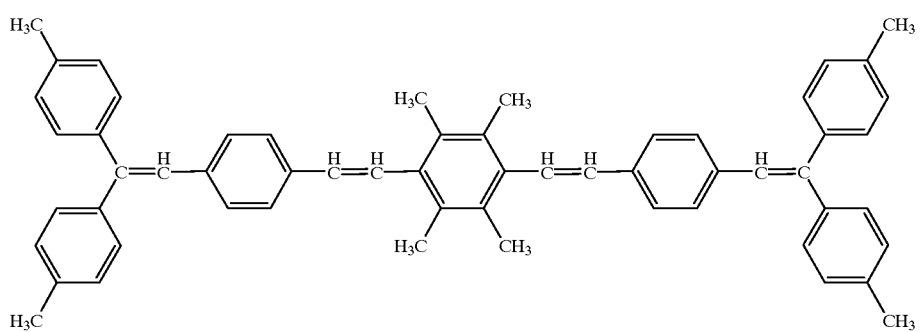

-continued
(Compound No. 17)
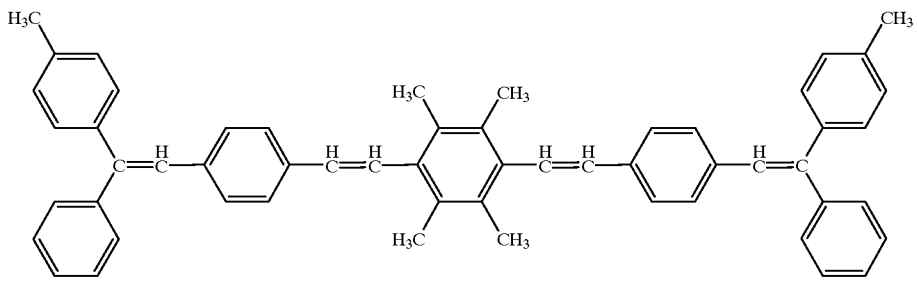
(Compound No. 18)
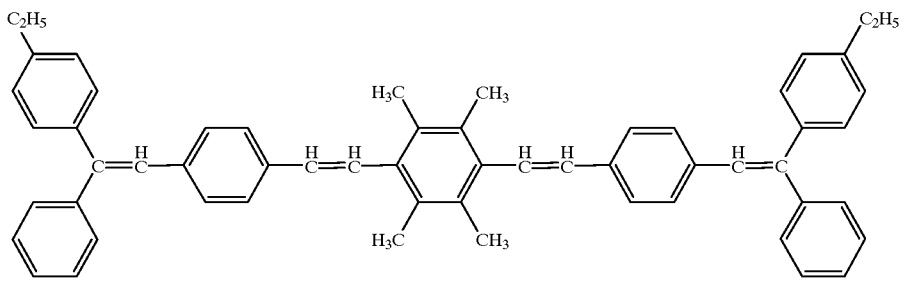
(Compound No. 19)
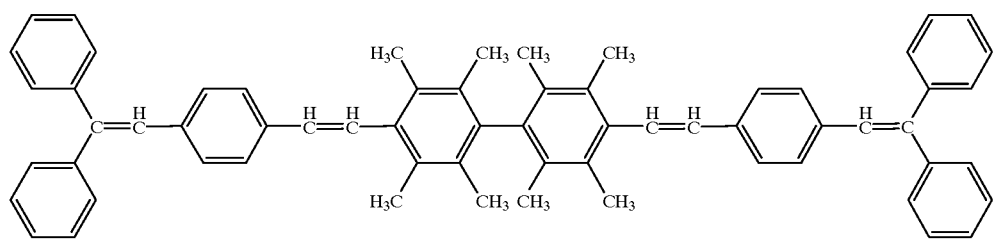
(Compound No. 20)
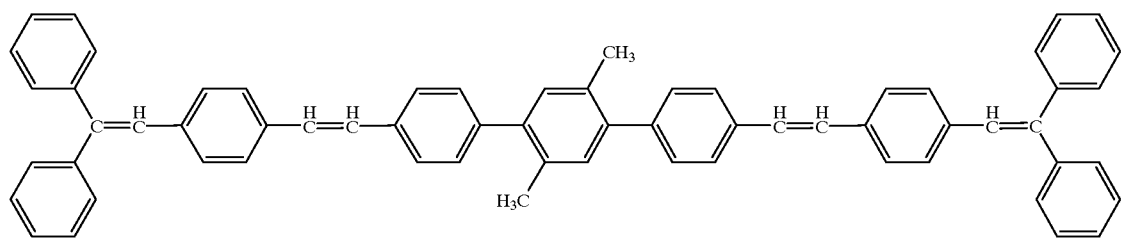
(formula 7)
(Compound No. 21)
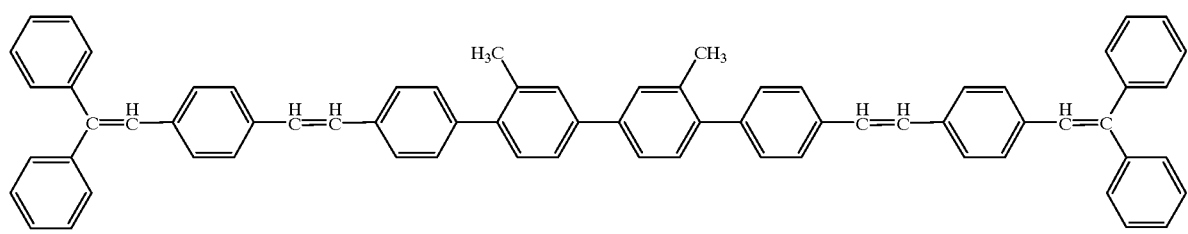

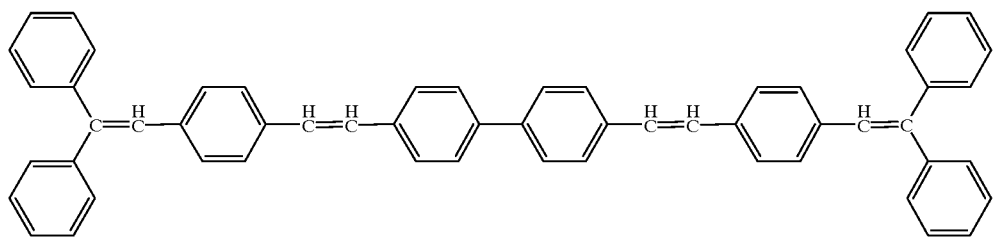
(Compound No. 22)
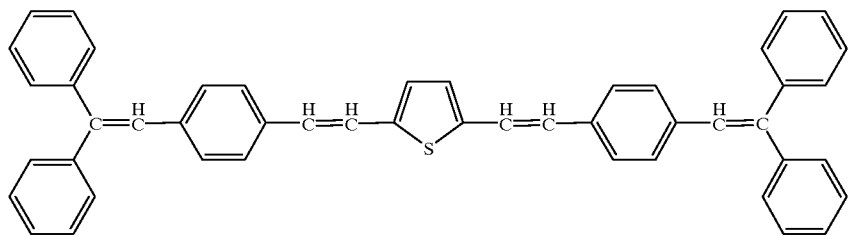
(Compound No. 23)
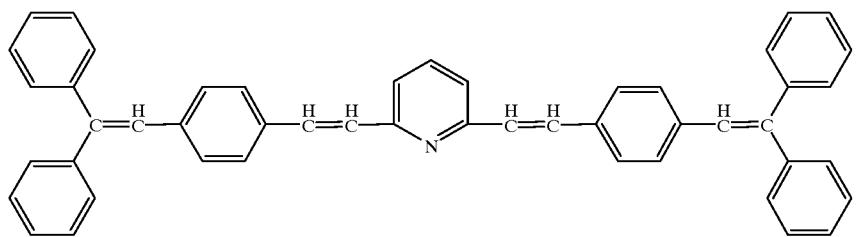
(Compound No. 24)
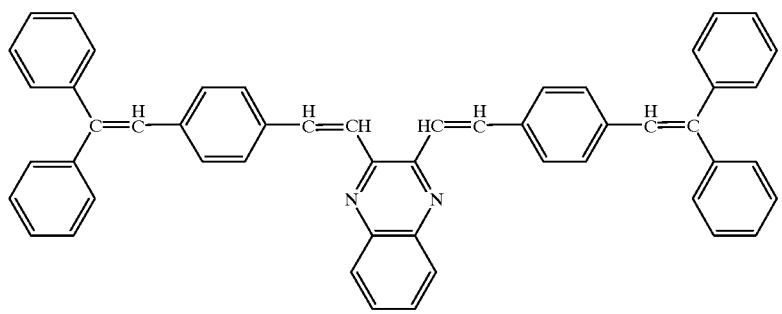
(Compound No. 25)
(formula 8)
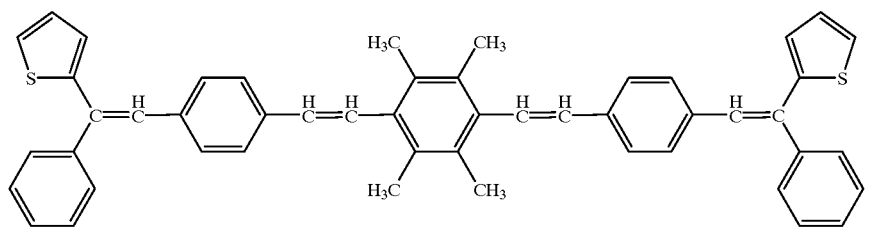
(Compound No. 26)
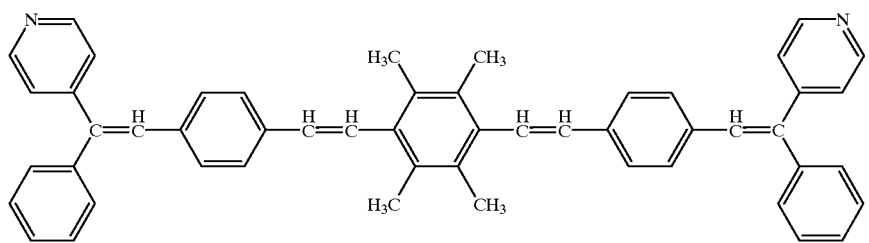
(Compound No. 27)

-continued
(Compound No. 28)
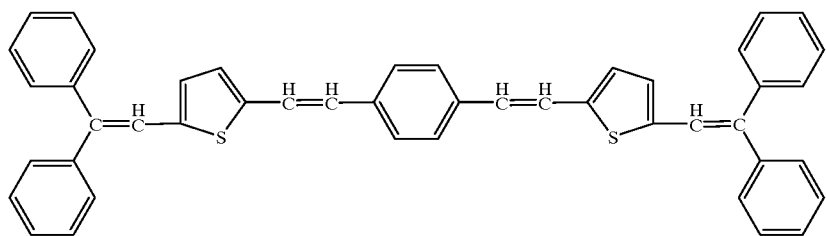
(Compound No. 29)
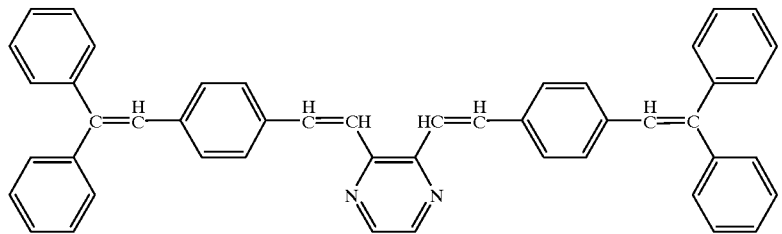
(Compound No. 30)
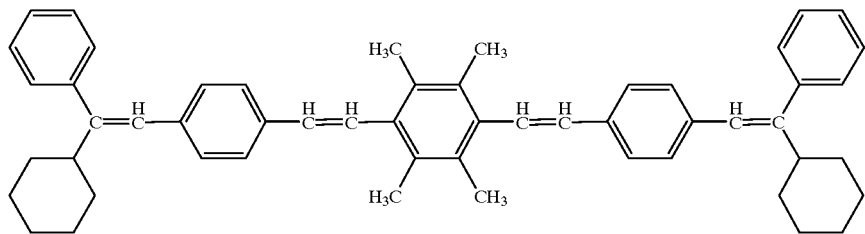
(formula 9)
(Compound No. 31)
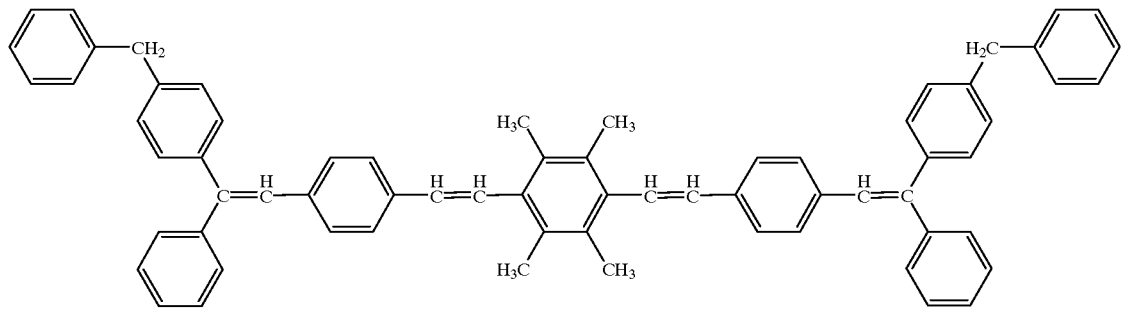
(Compound No. 32)
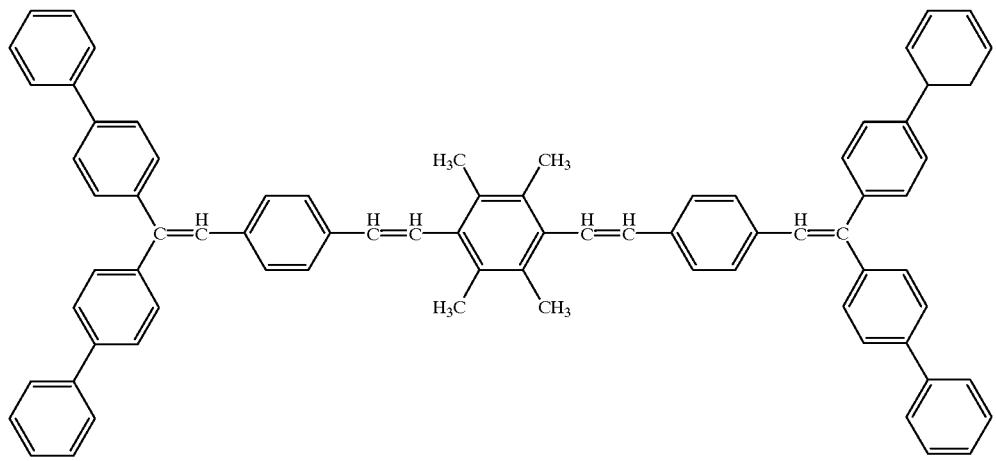

-continued
(Compound No. 33)
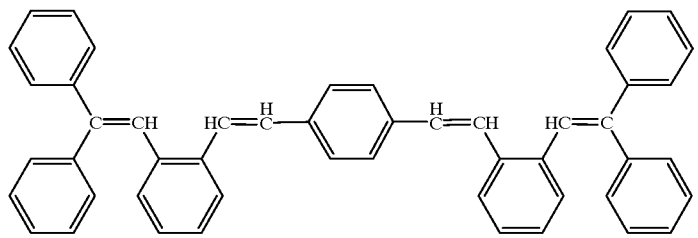
(Compound No. 34)
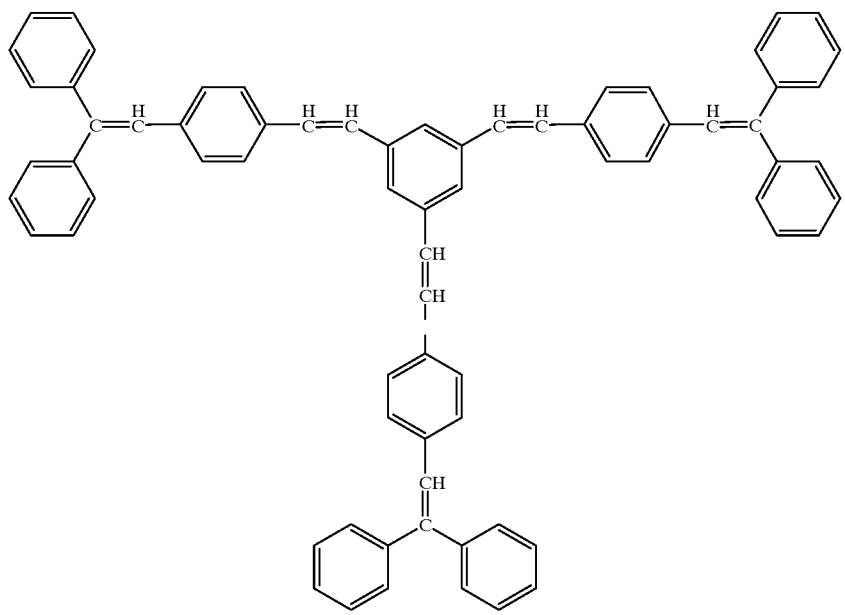
(formula 10)
(Compound No. 35)
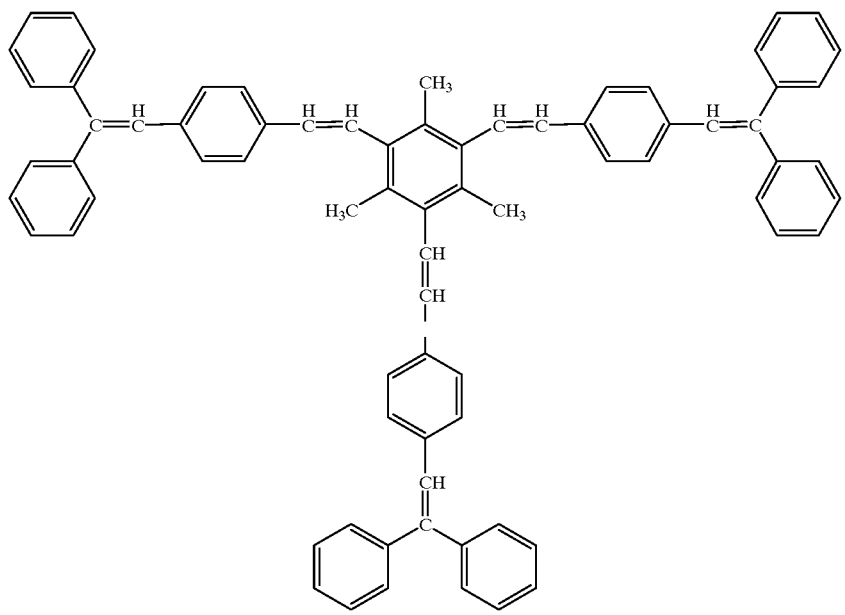

-continued
(Compound No. 36)
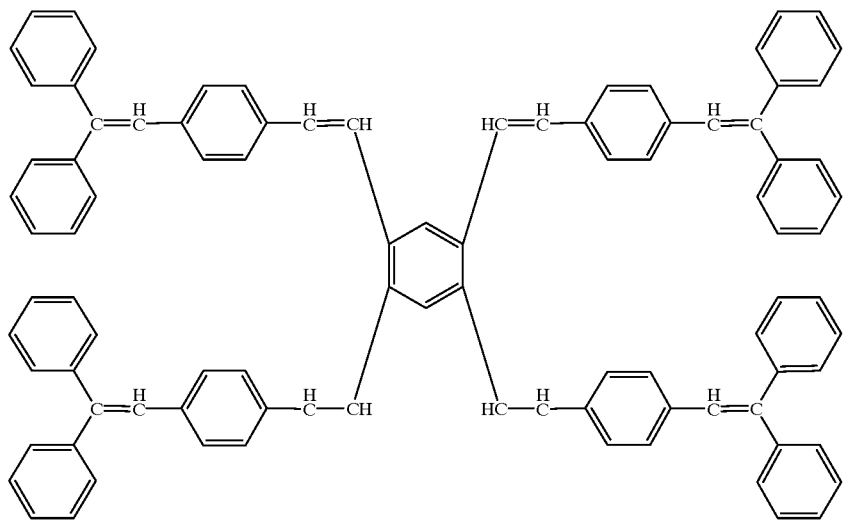
(Compound No. 37)
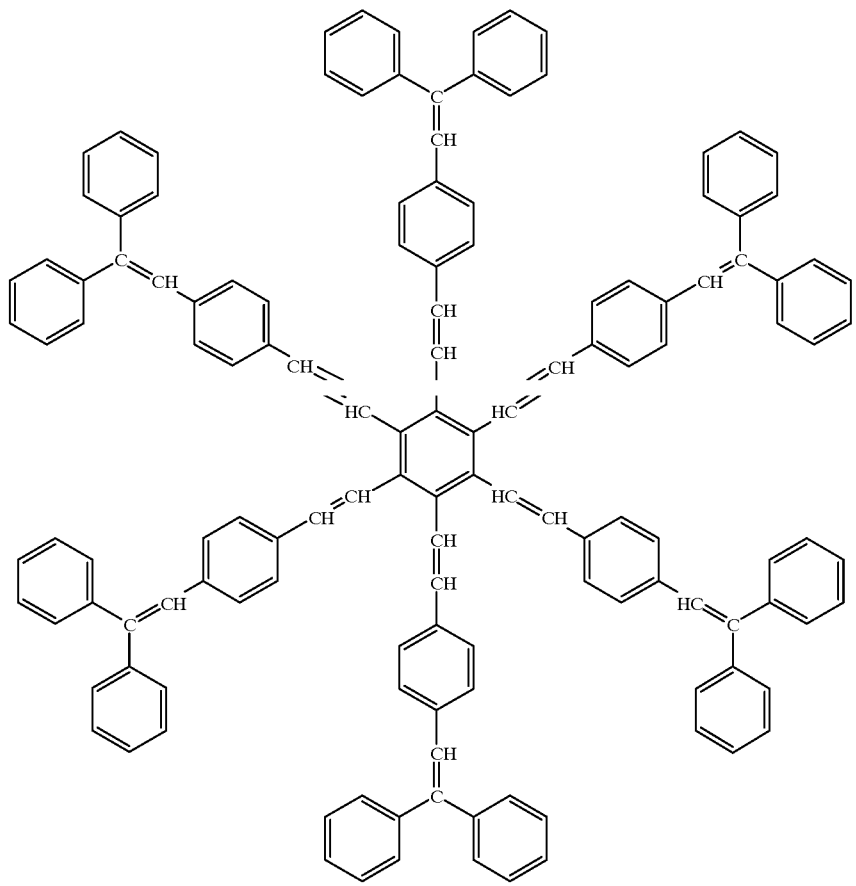

(formula 11)

(Compound No. 38)

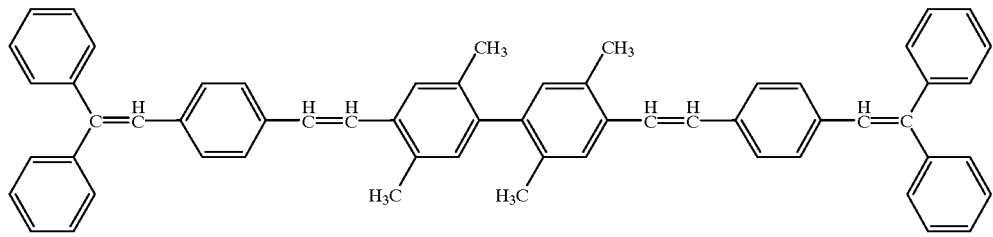

(Compound No. 39)

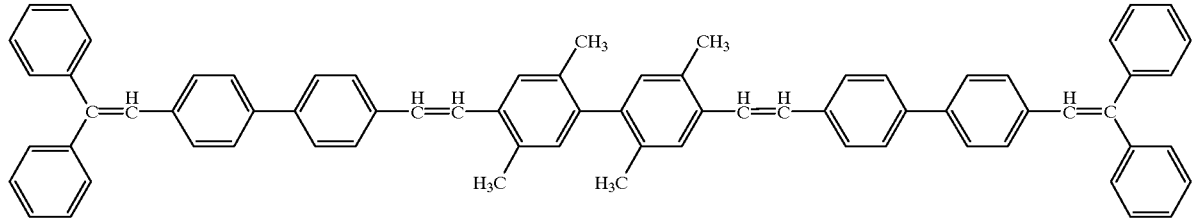

(Compound No. 40)

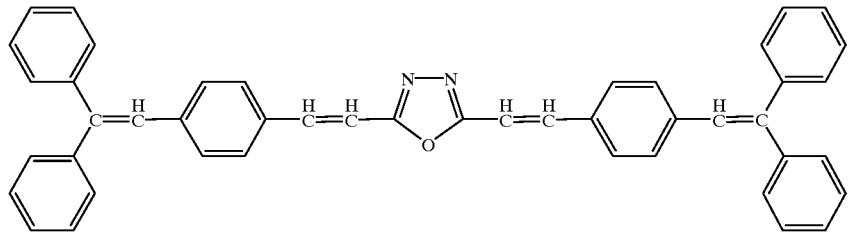

(Compound No. 41)

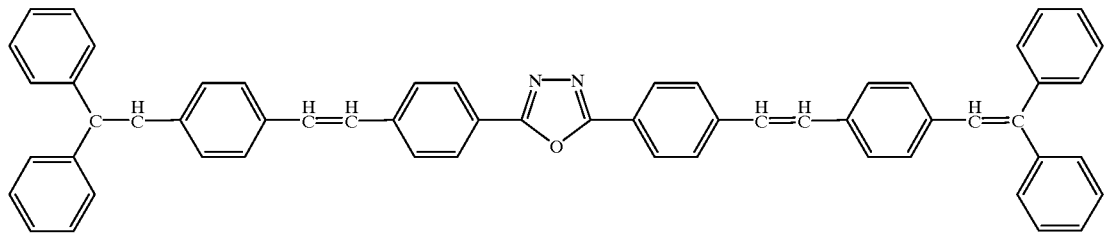

In the present organic electroluminescent component, the form of the aromatic methylidene compound represented by the aforesaid general formula is not restricted to particular ones when used. The present organic electroluminescent component comprises a thin film layer, in which at least the aromatic methylidene compound represented by the aforesaid general formula is present, interposed between a pair of electrodes.

Figure 2:
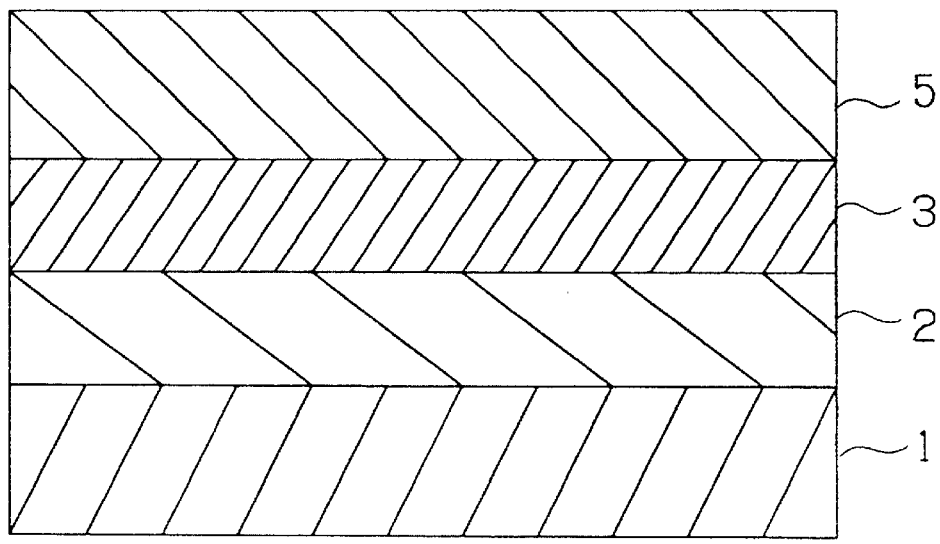
FIG. 2 is a schematic sectional view of a component consisting of a cathode, a positive hole-transporting layer, a luminescent layer and an anode, which is one embodiment of the present invention.
Figure 3:
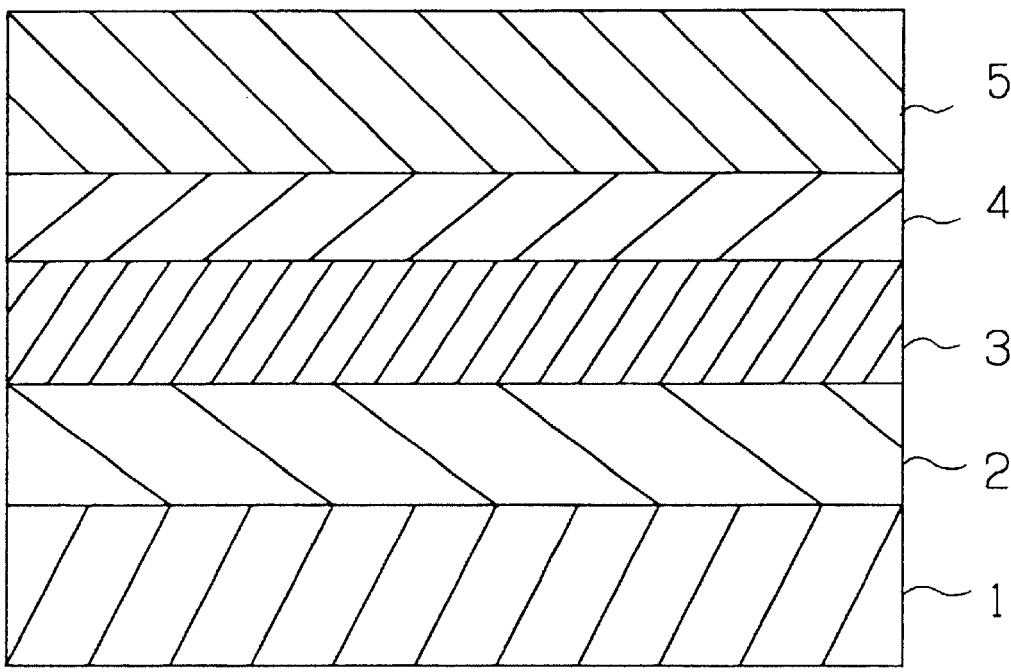
FIG. 3 is a schematic sectional view of a component consisting of a cathode, a positive hole-transporting layer, a luminescent layer, an electron-transporting layer and an anode, which is one embodiment of the present invention.
Figure 4:
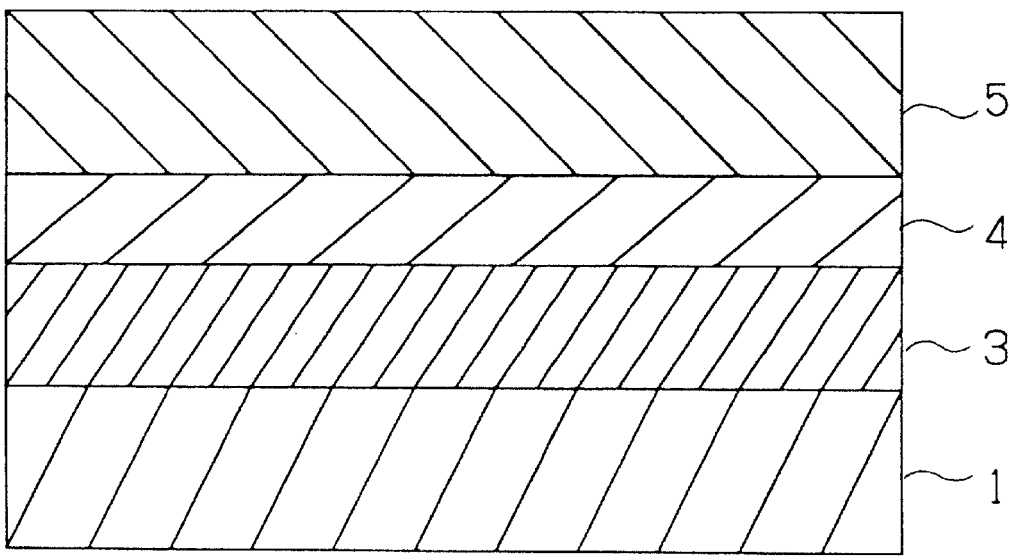
FIG. 4 is a schematic sectional view of a component consisting of a cathode, a luminescent layer, an electron-transporting layer and an anode, which is one embodiment of the present invention.

Although the organic electroluminescent component using the aromatic methylidene compound according to the invention may have various constructions, the basic construction has a luminescent layer interposed between a pair of electrodes (cathode and anode). If needed, a positive hole-transporting layer and an electron-transporting layer may be added to this construction. Concretely, use may be made of the component having the following constructions: (1) cathode/luminescent layer/anode shown in FIG. 1; (2) cathode/positive hole-transporting layer/luminescent layer/anode shown in FIG. 2; (3) cathode/positive hole-transporting layer/luminescent layer/electron-transporting layer/anode shown in FIG. 3; and (4) cathode/luminescent layer/electron-transporting layer/anode shown in FIG. 4. The positive hole-transporting layer and the electron-transporting layer are not essential, but it is preferred to have these layers because they make luminescent properties of the component improved in many cases. In either construction, basically, the component is preferably supported by a substrate. Each constituent will be described more specifically below.

First, the substrate is not restricted to particular ones. Mention may be made of glasses, transparent plastics or quartz. According to the necessity for construction of the component, a material for the substrate is selected and its thickness and form are determined properly.

As the anode, use may be made of metals, alloys, electroconductive compounds and a mixture thereof which have comparatively high work function (at least 4 eV). Examples of the anode materials include metals such as Au or dielectric transparent materials such as CuI, ITO, $SnO_2$ and ZnO. The anode may be formed generally as a thin film by a vapor deposition or sputtering method. Sheet resistance as an electrode is preferably not more than several hundred ohms/ square. The thickness, which depends on materials, is generally selected in a range of about 10 nm to 500 nm, preferably about 20 nm to 300 nm.

As the cathode, use may be made of metals, alloys, electroconductive compounds and a mixture thereof which have comparatively low work function (at most 4 eV). Examples of the cathode materials include sodium, sodium-potassium alloy, magnesium, lithium, magnesium/copper mixture, Al/AlO$_2$ and indium. The cathode may be formed as a thin film by a vapor deposition or sputtering method as well. Sheet resistance as an electrode is preferably not more than several hundred ohms/square. The thickness is in a range of 50 nm to 1000 nm, preferably 100 nm to 500 nm.

The positive hole-transporting layer consists of a positive hole-transporting compound(s) and has a function of transporting and injecting the positive holes which are injected from the cathode to the luminescent layer. The positive hole-transporting compound is not restricted to particular ones as long as it has the aforesaid function. Any compound may be selected among materials which have been used as a positive hole-transporting material in organic photoconductive materials and the known materials used for a positive hole-transporting layer or organic electroluminescent components. Mention may be made of, for instance, triazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, oxazole derivatives, styrylanthracene derivatives, fluorenone derivatives, hydrazone derivatives, stilbene derivatives, porphyrin compounds, aromatic tertiary amine compounds and styrylamine compounds. The positive hole-transporting layer may be one layer composed of one or more of these positive hole transporting compounds. Alternatively, it may be a laminate of the aforesaid layer and the layer composed of another positive hole-transporting compound(s). The positive hole-transporting layer may be formed by a vapor deposition or spin-coating method which is generally used for forming films. The thickness is generally 10 nm to 1 µm, preferably 20 nm to 500 nm.

The electron-transporting layer consists of an electron-transporting compound(s) and has a function of transporting and injecting the electrons which are injected from the anode to the luminescent layer. For the electron-transporting compound, any compound may be selected among the known compounds. Examples of the electron-transporting compound include nitro-substituted fluorenone derivatives, thiopyranedioxide derivatives, diphenoquinone derivatives, anthraquinodimethane derivatives, fluorenylidenemethane derivatives and anthrone derivatives. The electron-transporting layer may be one layer composed of one or more of these electron-transporting compounds. Alternatively, it may be a laminate of the aforesaid layer and the layer composed of another electron-transporting compound(s). The electron-transporting layer may be formed by a vapor deposition of spin-coating method which is generally used for forming films as well. The thickness is generally 10 nm to 1 µm, preferably 20 nm to 500 nm.

The positive hole-transporting layer and the electron-transporting layer have functions such as injection, transportation and barrier of electric charge. In addition to the aforesaid organic materials, Si type, SiC type or CdS type inorganic materials may be used. The positive hole-transporting layer and the electron-transporting layer using the inorganic materials may be formed by a vacuum vapor deposition or sputtering method.

The luminescent layer has a function that electrons and positive holes which are injected from electrodes or the positive hole-transporting layer or the electron-transporting layer recombine to cause luminescence. The aromatic methylidene compound according to the invention is suitably used particularly for the luminescent layer. The aromatic methylidene compound according to the invention is used mainly in this layer. The luminescent layer according to the invention may be one layer composed of one or more of these compounds. Alternatively, it may be a laminate of the aforesaid layer and the layer composed of another compound(s). Of course, use may be made of a combination of the aromatic methylidene compound according to the invention and a known luminescent material, if needed.

The luminescent layer may have the so-called "guest-host" constitution where a comparatively small amount of a guest compound is added (or doped) to a host compound. In the luminescent layer of the guest-host constitution, luminescence is generated mainly from the guest compound. In this luminescent layer of the guest-host constitution, it is preferred that the guest compound has a smaller energy gap and greater fluorescence compared to the host compound. This type of the guest compound includes various fluorescent dyes and laser colorants. Among them, coumarin derivatives and condensed ring compounds are preferable. This constitution can contribute to improvements in luminescent efficiency and driving resistance of the component. The aromatic methylidene compound according to the invention is effective as the host compound in combination with the aforesaid guest compounds or as the guest compound in combination with the known guest compounds in the luminescent layer of the guest-host constitution. The present invention includes the aforesaid idea. The concentration of the guest compound to the host compound may be within the range that concentration quenching does not happen. Preferably, it may be used in the range of about 0.01 to 40 mole %. It is also possible to use the luminescent layer obtained by stacking a layer comprising a mixture of the host compound with the guest compound as a main ingredient and a layer consisting of another luminescent material or stacking a layer comprising a combination of the host compound and the guest compound as a main ingredient and a layer comprising another combination of those as a main ingredient.

The luminescent layer may be formed by a vapor deposition or spin-coating method which is generally used for forming films as well. The thickness is generally 10 nm to 500 nm, preferably 20 nm to 200 nm.

EXAMPLES

Then, the present invention will be described more specifically with reference to the Examples.

Example 1

The present organic electroluminescent component was prepared by forming a positive hole-transporting layer, a luminescent layer, an electron-transporting layer and an aluminum/lithium (Al/Li) electrode as an anode successively by vapor deposition on a glass substrate on which a thin film of indium tin oxide (ITO), which is a transparent electrode, has been formed as an anode (ITO glass substrate). Specifically, first, an ITO glass substrate, N,N'-diphenyl-N,N'-bis(3-methylphenyl)benzidine (TPD) as a material for transporting positive holes, the aromatic methylidene compound of the invention, Compound No. 1, as a luminescent material and tris(8-hydroxyquinolino) aluminum (Alq) as a material for transporting electrons were set in a vacuum vapor deposition apparatus. The apparatus was evacuated to $10^{-4}$ Pa. Secondly, TPD as a material for transporting positive holes was vapor deposited on the ITO glass substrate as a deposition rate of 0.1 to 0.5 nm/sec. to form a positive hole-transporting layer with a thickness of 50 nm. Next, Compound No. 1 as a luminescent material was vapor deposited thereon at a deposition rate of 0.1 to 0.5 nm/sec. to form a luminescent layer with a thickness of 50 nm. Subsequently, Alq as a material for transporting electrons was vapor deposited thereon at a deposition rate of 0.1 nm/sec. to form an electron-transporting layer with a thickness of 10 nm. Then, the vapor deposition was further carried out at a rate of 0.5 nm/sec. to form an Al/Li electrode with a thickness of 150 nm. All of the aforesaid vapor deposition was carried out successively without breaking vacuum. The thickness was controlled by monitoring it with a quartz oscillator. After the vapor deposition, the resultant component was immediately taken out in a dry nitrogen atmosphere to obtain the organic electroluminescent component of the invention. When voltage was applied to the component thus obtained, homogeneous blue luminescence was obtained. The emission spectrum has a peak on a wavelength of 480 nm. Determination of driving voltage and luminescent brightness in 100 mA/cm$^2$ electric current application gave a driving voltage of 7.5 V and a luminescent brightness of 2400 cd/m$^2$. As a measure of the life of this component, half-life time of luminescent brightness was determined by continuously driving the component while applying a constant current of 20 mA/cm$^2$. As a result, the brightness was reduced by half for 200 hours.

Next, for comparison to the prior art luminescent materials, the same procedures as in Example 1 were carried out to obtain a component, except that 4,4'-bis(2,2-diphenylvinyl)biphenyl described in Japanese Patent Application Laid-Open No. Hei-3-231970 was used in stead of the luminescent material in Example 1. Application of the voltage to the resultant component gave homogeneous blue luminescence. The emission spectrum has a peak on a wavelength of 450 nm. Application of 100 mA/cm$^2$ current to the component gave a driving voltage of 6 V and a luminescent brightness of 1200 cd/m$^2$. As a measure of the life of this component, half-life time of luminescent brightness was determined by continuously driving the component while applying constant current of 20 mA/cm$^2$. As a result, after three hours passed, aggregation happened on a part of the organic film to cause electric short circuit between the electrodes and, therefore, the luminescence stopped.

Example 2

The same procedure as in Example 1 were carried out to obtain an organic electroluminescent component, except that Compound No. 2 was used in stead of Compound No. 1 in Example 1. Application of the voltage to the resultant component gave homogeneous blue luminescence. The emission spectrum had a peak on a wavelength of 480 nm. Application of 100 mA/cm$^2$ current to the component gave a driving voltage of 7.0 V and a luminescent brightness of 2300 cd/m$^2$. As a measure of the life of this component, half-life time of luminescent brightness was determined by continuously driving the component while applying constant current of 20 mA/cm$^2$. As a result, the brightness was reduced by half for 200 hours.

Example 3

The same procedures as in Example 1 were carried out to obtain an organic eletroluminescent component, except that Compound No. 3 was used in stead of Compound No. 1 in Example 1. Application of the voltage to the resultant component gave homogeneous green luminescence. The emission spectrum had a peak on a wavelength of 545 nm.

Example 4

The same procedures as in Example 1 were carried out to obtain an organic electroluminescent component, except that Compound No. 4 was used in stead of Compound No. 1 in Example 1. Application of the voltage to the resultant component gave homogeneous blue luminescence.

Example 5

The same procedures as in Example 1 were carried out to obtain an organic electroluminescent component, except that Compound No. 5 was used in stead of Compound No. 1 in Example 1. Application of the voltage to the resultant component gave homogeneous bluish green luminescence.

Example 6

The same procedures as in Example 1 were carried out to obtain an organic electroluminescent component, except that Compound No. 7 was used in stead of Compound No. 1 in Example 1. Application of the voltage to the resultant component gave homogeneous bluish green luminescence.

Example 7

The same procedures as in Example 1 were carried out to obtain an organic electroluminescent component, except that Compound No. 9 was used in stead of Compound No. 1 in Example 1. Application of the voltage to the resultant component gave homogeneous blue luminescence.

Example 8

The same procedures as in Example 1 were carried out to obtain an organic electroluminescent component, except that Compound No. 10 was used in stead of Compound No. 1 in Example 1. Application of the voltage to the resultant component gave homogeneous blue luminescence.

Example 9

The same procedures as in Example 1 were carried out to obtain an organic electroluminescent component, except that Compound No. 11 was used in stead of Compound No. 1 in Example 1. Application of the voltage to the resultant component gave homogeneous bluish green luminescence.

Example 10

The same procedures as in Example 1 were carried out to obtain an organic electroluminescent component, except that Compound No. 12 was used in stead of Compound No. 1 in Example 1. Application of the voltage to the resultant component gave homogeneous blue luminescence.

Example 11

The same procedures as in Example 1 were carried out to obtain an organic electroluminescent component, except that Compound No. 14 was used in stead of Compound No. 1 in Example 1. Application of the voltage to the resultant component gave homogeneous blue luminescence.

Example 12

The same procedures as in Example 1 were carried out to obtain an organic electroluminescent component, except that Compound No. 15 was used in stead of Compound No. 1 in Example 1. Application of the voltage to the resultant component gave homogeneous blue luminescence.

Example 13

The same procedures as in Example 1 were carried out to obtain an organic electroluminescent component, except that Compound No. 16 was used in stead of Compound No. 1 in Example 1. Application of the voltage to the resultant component gave homogeneous blue luminescence.

Example 14

The same procedures as in Example 1 were carried out to obtain an organic electroluminescent component, except that Compound No. 17 was used in stead of Compound No. 1 in Example 1. Application of the voltage to the resultant component gave homogeneous blue luminescence.

Example 15

The same procedures as in Example 1 were carried out to obtain an organic electroluminescent component, except that Compound No. 18 was used in stead of Compound No. 1 in Example 1. Application of the voltage to the resultant component gave homogeneous blue luminescence.

Example 16

The same procedures as in Example 1 were carried out to obtain an organic electroluminescent component, except that Compound No. 19 was used in stead of Compound No. 1 in Example 1. Application of the voltage to the resultant component gave homogeneous blue luminescence.

Example 17

The same procedures as in Example 1 were carried out to obtain an organic electroluminescent component, except that Compound No. 20 was used in stead of Compound No. 1 in Example 1. Application of the voltage to the resultant component gave homogeneous blue luminescence.

Example 18

The same procedures as in Example 1 were carried out to obtain an organic electroluminescent component, except that Compound No. 21 was used in stead of Compound No. 1 in Example 1. Application of the voltage to the resultant component gave homogeneous blue luminescence.

Example 19

The same procedures as in Example 1 were carried out to obtain an organic electroluminescent component, except that Compound No. 23 was used in stead of Compound No. 1 in Example 1. Application of the voltage to the resultant component gave homogeneous green luminescence.

Example 20

The same procedures as in Example 1 were carried out to obtain an organic electroluminescent component, except that Compound No. 27 was used in stead of Compound No. 1 in Example 1. Application of the voltage to the resultant component gave homogeneous blue luminescence.

Example 21

The same procedures as in Example 1 were carried out to obtain an organic electroluminescent component, except that Compound No. 30 was used in stead of Compound No. 1 in Example 1. Application of the voltage to the resultant component gave homogeneous blue luminescence.

Example 22

The same procedures as in Example 1 were carried out to obtain an organic electroluminescent component, except that Compound No. 31 was used in stead of Compound No. 1 in Example 1. Application of the voltage to the resultant component gave homogeneous bluish green luminescence.

Example 23

The same procedures as in Example 1 were carried out to obtain an organic electroluminescent component, except that Compound No. 32 was used in stead of Compound No. 1 in Example 1. Application of the voltage to the resultant component gave homogeneous bluish green luminescence.

Example 24

The same procedures as in Example 1 were carried out to obtain an organic electroluminescent component, except that Compound No. 34 was used in stead of Compound No. 1 in Example 1. Application of the voltage to the resultant component gave homogeneous yellowish green luminescence.

Example 25

The same procedures as in Example 1 were carried out to obtain an organic electroluminescent component, except that Compound No. 35 was used in stead of Compound No. 1 in Example 1. Application of the voltage to the resultant component gave homogeneous blue luminescence.

Example 26

The present organic electroluminescent component was prepared by forming a positive hole-transporting layer, a luminescent layer and an anode on a cathode of an ITO glass substrate. Specifically, the ITO glass substrate, TPD as a material for transporting positive holes and Compound No. 1 as a luminescent material were set in a vacuum vapor deposition apparatus. The apparatus was evacuated to $10^{-4}$ Pa. Then, a positive hole-transporting layer with a thickness of 50 nm was formed on the cathode of the ITO glass substrate. Next, Compound No. 1 was vapor deposited thereon to form a luminescent layer with a thickness of 50 nm. Subsequently, an Al/Li electrode with a thickness of 150 nm was formed. All of the aforesaid vapor deposition was carried out successively without breaking vacuum. The thickness was controlled by monitoring it with a quartz oscillator. After the vapor deposition, the resultant component was immediately taken out in dry nitrogen to obtain the organic electroluminescent component of the invention. When voltage was applied to the component thus obtained, homogeneous blue luminescence was obtained. The driving voltage was 8 V and the luminescent brightness was 1800 $cd/m^2$.

Example 27

The present organic electroluminescent component was prepared by forming a luminescent layer and an anode on a cathode of an ITO glass substrate. Specifically, the ITO glass substrate and Compound No. 1 as a luminescent material were set in a vacuum vapor deposition apparatus. The apparatus was evacuated to $10^{-4}$ Pa. Next, a layer of Compound No. 1 with a thickness of 100 nm was formed on the cathode of the ITO glass substrate. Subsequently, an Al/Li electrode with a thickness of 150 nm was formed. All of the aforesaid vapor deposition was carried out successively without breaking vacuum. The thickness was controlled by monitoring it with a quartz oscillator. After the vapor deposition, the resultant component was immediately taken out in dry nitrogen to obtain the organic electroluminescent component of the invention. When voltage was applied to the component thus obtained, homogeneous blue luminescence was obtained. The driving voltage was 9.7 V and the luminescent brightness was 950 $cd/m^2$.

Example 28

The present organic electroluminescent component was prepared by forming a luminescent layer, an electron-transporting layer and an anode on a cathode of an ITO glass substrate. Specifically, the ITO glass substrate, Compound No. 1 as a luminescent material and 2-(biphenyl-4-yl)-5-(4-tert-butylphenyl)-1,3,4-oxadiazole as a material for transporting electrons were set in a vacuum vapor deposition apparatus. The apparatus was evacuated to $10^{-4}$ Pa. Then, a layer of Compound No. 1 with a thickness of 50 nm, as a luminescent layer, was formed on the cathode of the ITO glass substrate. Subsequently, an electron-transporting layer with a thickness of 50 nm was formed. Next, an Al/Li electrode with a thickness of 150 nm was formed. All of the aforesaid vapor deposition was carried out successively without breaking vacuum. The thickness was controlled by monitoring it with a quartz oscillator. After the vapor deposition, the resultant component was immediately taken out in dry nitrogen to obtain the organic electroluminescent component of the invention. When voltage was applied to the component thus obtained, homogeneous blue luminescence was obtained. The driving voltage was 8.9 V and the luminescent brightness was 600 cd/m².

Example 29

The present organic electroluminescent component was prepared by forming a positive hole-transporting layer, a luminescent layer and an anode on a cathode of an ITO glass substrate. Specifically, the ITO glass substrate, TPD as a material for transporting positive holes, Compound No. 1 as a host compound and the compound represented by the following formula, hereinafter referred to as EM-1, as a guest compound were set in a vacuum vapor deposition apparatus. The apparatus was evacuated to $10^{-4}$ Pa. Then, a positive hole-transporting layer with a thickness of 50 nm was formed on the cathode of the ITO glass substrate. Next, Compound No. 1 and EM-1 were co-deposited to form a film with a thickness of 50 nm as a luminescent layer. A concentration ratio of EM-1 to Compound No. 1 was 3 mole %. Next, an Al/Li electrode with a thickness of 150 nm was formed. All of the aforesaid vapor deposition was carried out successively without breaking vacuum. The thickness was controlled by monitoring it with a quartz oscillator. After the vapor deposition, the resultant component was immediately taken out in dry nitrogen to obtain the organic electroluminescent component of the invention. When voltage was applied to the component thus obtained, homogeneous bluish green luminescence was obtained. The driving voltage was 8.5 V and the luminescent brightness was 3100 cd/m². When this component was continuously driven in dry nitrogen at an initial brightness of 1000 cd/m², it took 750 hours to decrease the brightness to a half of the initial brightness, i.e. 500 cd/m².

Example 30

After an ITO glass substrate was set in a vacuum vapor deposition apparatus which was then evacuated to $10^{-4}$ Pa, a film of TPD with a thickness of 50 nm was formed as a positive hole-transporting layer. Then, Compound No. 1 as a host compound and rubrene as a guest compound for a luminescent layer were co-deposited to form a film with a thickness of 25 nm as a luminescent layer. A concentration ratio of rubrene to Compound No. 1 was 5 mole %. Next, a film of Alq with a thickness of 25 nm as an electron-transporting layer and an Al/Li electrode with a thickness of 150 nm as an anode were formed to prepare a component. These film-forming operations were carried out successively without breaking vacuum. The thickness was controlled by monitoring it with a quartz oscillator. After the film-forming operations, the resultant component was immediately taken out in dry nitrogen. Subsequently, the properties were determined. When voltage was applied to the component thus obtained, homogeneous yellow luminescence having a peak at 560 nm as obtained. Determination of driving voltage and luminescent brightness in 100 mA/cm² electric current application gave a driving voltage of 7 V and a luminescent brightness of 4000 cd/m². When this component was continuously driven in dry nitrogen at an initial brightness of 1000 cd/m², time for decreasing the brightness to a half of the initial brightness, i.e. 500 cd/m², (brightness half-life) was 1230 hours.

Examples 31 to 36

The same procedures were carried out as in Example 30 to prepare an organic electroluminescent component, except that use were made of perylene in Example 31, 3-(2-benzothiazolyl)-7-(N,N-diethylamino)coumarin, hereinafter referred to as coumarin 6, in Example 32, 3-(benzoimidazoryl)-7-(N,N-diethylamino)coumarin, hereinafter referred to as coumarin 7, in Example 33, EM-1 in Example 34, the compound represented by the following formula, hereinafter referred to as EM-2, in Example 35 and 4-dicyanomethylene-2-methyl-6-(4-dimethylaminostyryl)-4 H-pyrane, hereinafter referred to as DCM, in Example 36, instead of rubrene as the guest compound for the luminescent layer in Example 30. The luminescent peak wavelength, driving voltage and luminescent brightness in 100 mA/cm² current application and brightness half-life when driven at an initial brightness of 1000 cd/m², of the components prepared in these Examples, were shown in Table 1 together with the results of Example 30.

(formula 12)

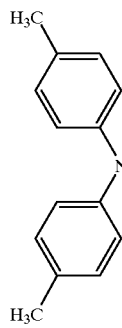

(EM-1)

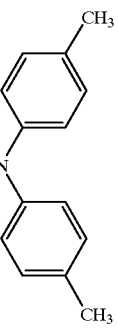

TABLE 1

| Ex. No. | Luminescent layer | | Luminescent | | | |
|---|---|---|---|---|---|---|
| | Guest compound | Host compound | Luminescence peak wavelength, nm | Driving voltage, V | brightness, $cd/m^2$ | Brightness half-life, hour |
| Ex. 30 | Rubrene | Compound No. 1 | 560 | 7.0 | 4000 | 1230 |
| Ex. 31 | Perylene | | 460 | 8.0 | 2500 | 740 |
| Ex. 32 | coumarin 6 | | 480 | 7.2 | 3800 | 830 |
| Ex. 33 | coumarin 7 | | 500 | 7.3 | 2800 | 780 |
| Ex. 34 | EM-1 | | 490 | 7.8 | 3400 | 990 |
| Ex. 35 | EM-2 | | 510 | 7.7 | 2600 | 920 |
| Ex. 36 | DCM | | 600 | 7.1 | 2500 | 830 |

(formula 13)

(EM-2)

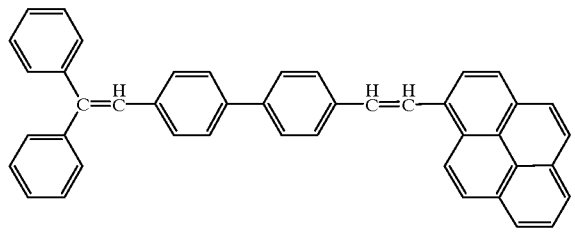

Examples 37 to 43

The same procedures were carried out as in Examples 30 to 36 to prepare an organic electroluminescent component, except that the host compound used for the luminescent layer was replaced with Compound No. 2. The luminescence peak wavelength, driving voltage and luminescent brightness in 100 mA/cm² current application and brightness half-life when driven at an initial brightness of 1000 cd/m², of the components prepared in these Examples, were shown in Table 2.

for a luminescent layer were co-deposited to form the luminescent layer with a thickness of 25 nm. A concentration ratio of Compound No. 3 to Compound No. 1 was mole %. Next, a film of Alq with a thickness of 25 nm as an electron-transporting layer and an Al/Li electrode with a thickness of 150 nm as an anode were formed to prepare a component. These film-forming operations were carried out successively without breaking vacuum. When voltage was applied to the component thus obtained, homogeneous bluish green luminescence having a peak at 490 nm was obtained. Determination of driving voltage and luminescent brightness in 100 mA/cm² electric current application gave a driving voltage of 6.9 V and a luminescent brightness of 3200 cd/m². When this component was continuously driven in dry nitrogen at an initial brightness of 1000 cd/m², the brightness half-life was 1150 hours.

Examples 45 to 46

The same procedures were carried out as in Example 44 to prepare an organic electroluminescent component, except that the guest compound used for the luminescent layer was changed. As the guest compound, use were made of the compound represented by the following formula, hereinafter

TABLE 2

| Ex. No. | Luminescent layer | | Luminescent | | | |
|---|---|---|---|---|---|---|
| | Guest compound | Host compound | Luminescence peak wavelength, nm | Driving voltage, v | brightness, $cd/m^2$ | Brightness half-life, hour |
| Ex. 37 | Rubrene | Compound No. 7 | 560 | 7.1 | 4300 | 1080 |
| Ex. 38 | Perylene | | 460 | 8.2 | 2900 | 580 |
| Ex. 39 | Coumarin 6 | | 480 | 7.3 | 3700 | 670 |
| Ex. 40 | Coumarin 7 | | 500 | 7.3 | 2800 | 610 |
| Ex. 41 | EM-1 | | 490 | 7.9 | 3500 | 800 |
| Ex. 42 | EM-2 | | 510 | 7.7 | 2600 | 740 |
| Ex. 43 | DCM | | 600 | 7.2 | 2400 | 650 |

Example 44

After an ITO substrate was set in a vacuum vapor deposition apparatus which was then evacuated to $10^{-4}$ Pa, a film of N,N'-bis[4'-(N,N-diphenylamino)-4-biphenylyl]-N,N'-diphenylbenzidine with a thickness of 50 nm was formed as a positive hole-transporting layer. Then, Compound No. 1 as a host compound and Compound No. 3 as a guest compound referred to as EM-3, in Example 45 and the compound represented by the following formula, hereinafter referred to as EM-4, in Example 46. The luminescence peak wavelength, driving voltage and luminescent brightness in 100 mA/cm² current application and brightness half-life when driven at an initial brightness of 1000 cd/m², of the components prepared in these Examples, were shown in Table 3 together with the results of Example 44.

TABLE 3

| Ex. No. | Luminescent layer | | Luminescence peak wavelength, nm | Driving voltage, v | Luminescent brightness, cd/m$^2$ | Brightness half-life, hour |
| --- | --- | --- | --- | --- | --- | --- |
| | Guest compound | Host compound | | | | |
| Ex. 44 | Compound No. 3 | Compound No. 1 | 490 | 6.9 | 3200 | 1150 |
| Ex. 45 | EM-3 | | 500 | 7.1 | 3000 | 1240 |
| Ex. 46 | EM-4 | | 500 | 6.8 | 3400 | 1280 |

(formula 14)

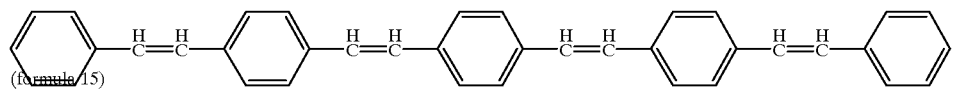

(EM-3)

(formula 15)

(EM-4)

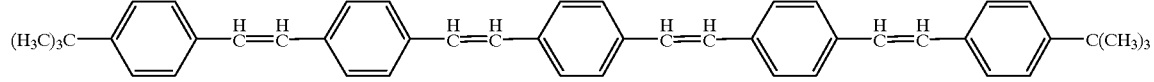

Examples 47 to 49

The same procedures were carried out as in Example 44 to 46 to prepare an organic electroluminescent component, except that the host compound used for the luminescent layer was replaced with the compound represented by the following formula, hereinafter referred to as EM-5. The luminescence peak wavelength, driving voltage and luminescent brightness in 100 mA/cm$^2$ current application and brightness half-life when driven at an initial brightness of 1000 cd/m$^2$, of the components prepared in these Examples, were shown in Table 4.

TABLE 4

| Ex. No. | Luminescent layer | | Luminescence peak wavelength, nm | Driving voltage, V | Luminescent brightness, cd/m$^2$ | Brightness half-life, hour |
| --- | --- | --- | --- | --- | --- | --- |
| | Guest compound | Host compound | | | | |
| Ex. 47 | Compound No. 3 | EM-5 | 490 | 7.5 | 2800 | 400 |
| Ex. 48 | EM-3 | | 500 | 7.5 | 2700 | 360 |
| Ex. 49 | EM-4 | | 500 | 7.3 | 2900 | 600 |

(formula 16)

(EM-5)

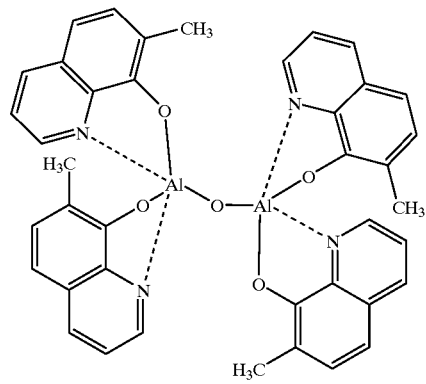

As mentioned above, the organic electroluminescent component of the invention in which the aromatic methylidene compound according to the invention is used is excellent in luminescent properties as well as in stability and has the long life, compared to the components in which the prior art compounds are used. Accordingly, the organic electroluminescent component of the invention can be utilized effectively in various industrial fields.

What is claimed is:

1. An organic electroluminescent material comprising a methylidene compound of the following general formula (1)

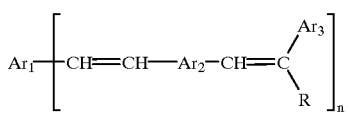

(1)

wherein Ar$_1$ represents a substituted or unsubstituted aromatic hydrocarbon residue having 2 to 6 valences, Ar$_2$ represents a divalent substituted or unsubstituted aromatic hydrocarbon residue, Ar$_3$ represents a substituted or unsubstituted aromatic hydrocarbon residue or a substituted or unsubstituted aromatic heterocyclic hydrocarbon residue, R represents a substituted or unsubstituted aromatic hydrocarbon residue, a substituted or unsubstituted aromatic heterocyclic hydrocarbon residue, a substituted or unsubstituted alkyl group provided that Ar$_3$ and R may join to form a ring, and n is an integer of 2 to 6.

2. An organic electroluminescent material according to claim 1, wherein said material consists of said methylidene compound.
3. An organic electroluminescent material according to claim 1, wherein said methylidene compound is a member selected from the group consisting of compounds of the following formulas
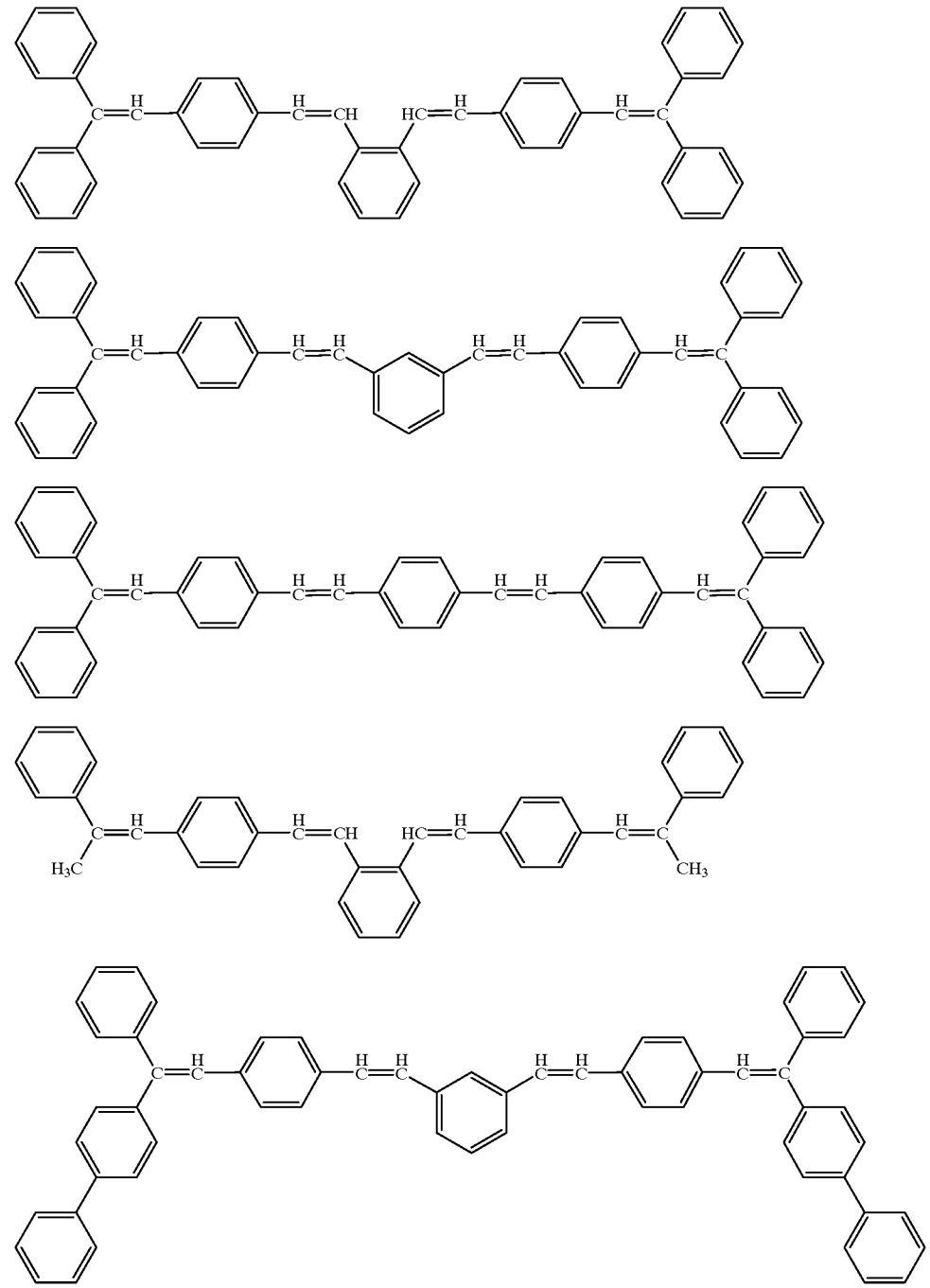

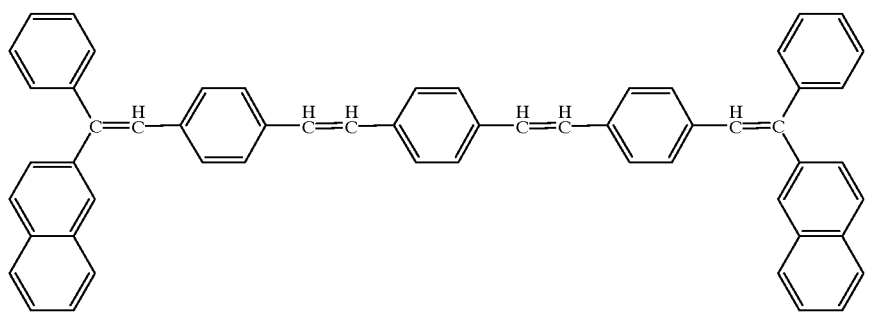
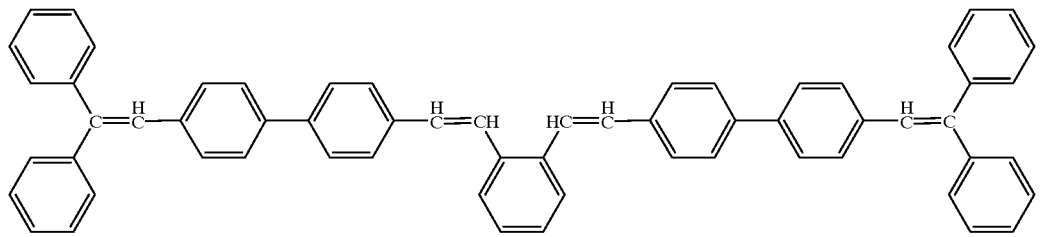
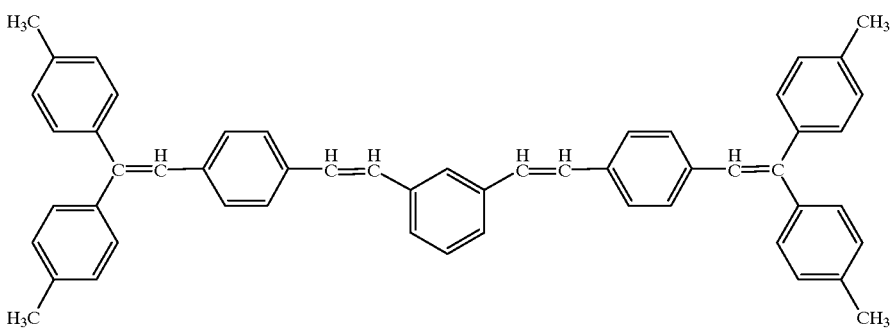
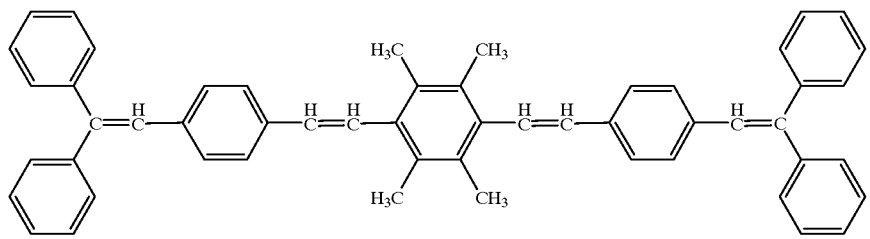
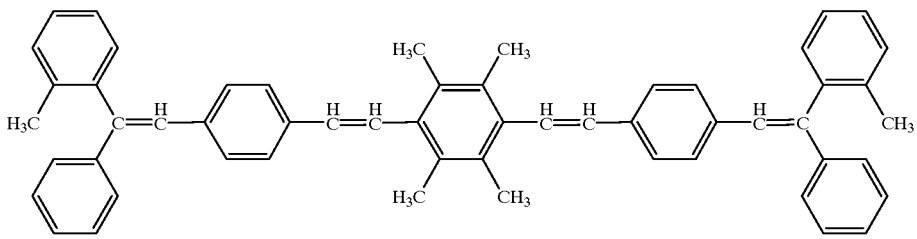
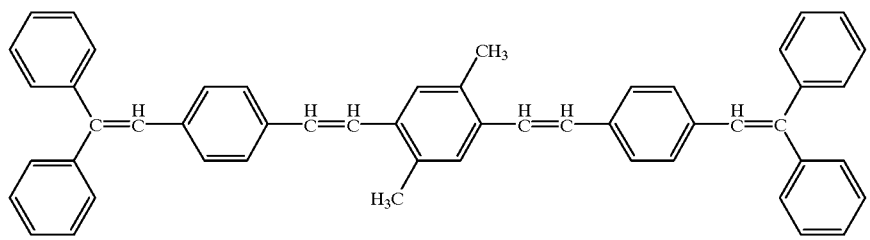

-continued
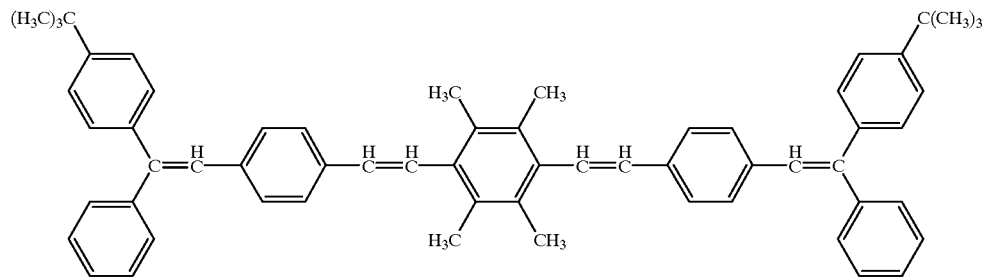
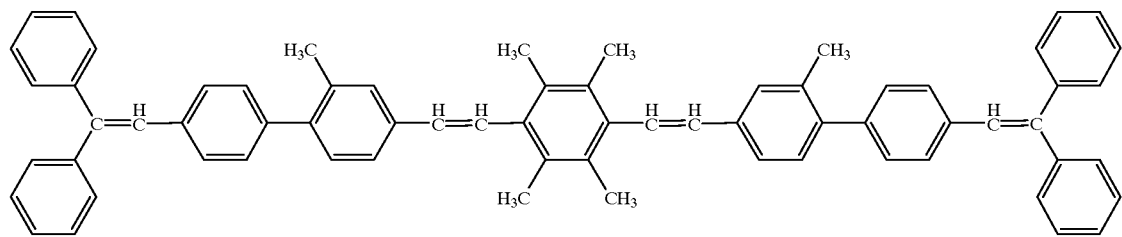
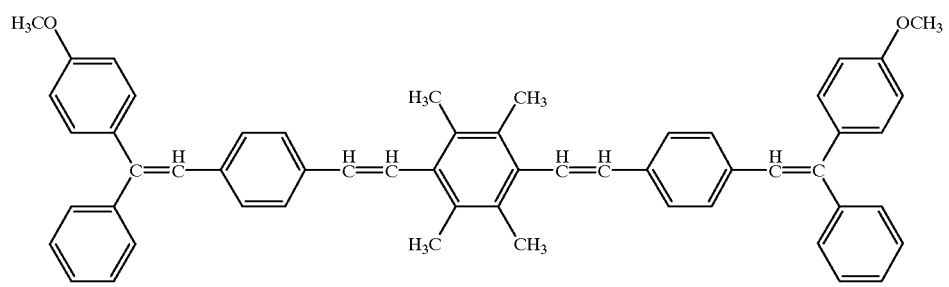
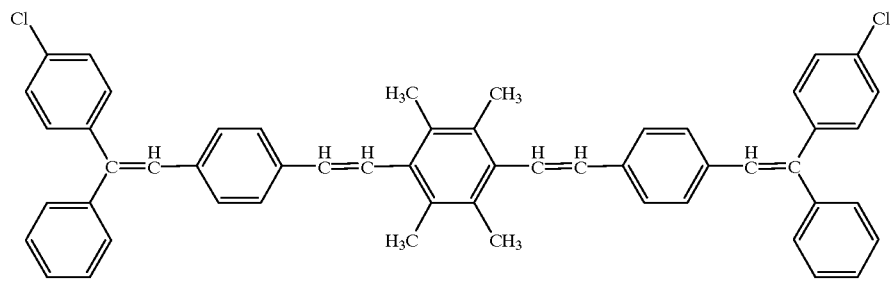
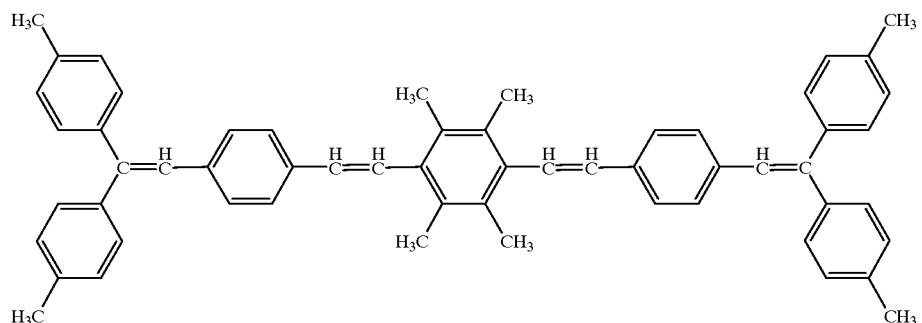
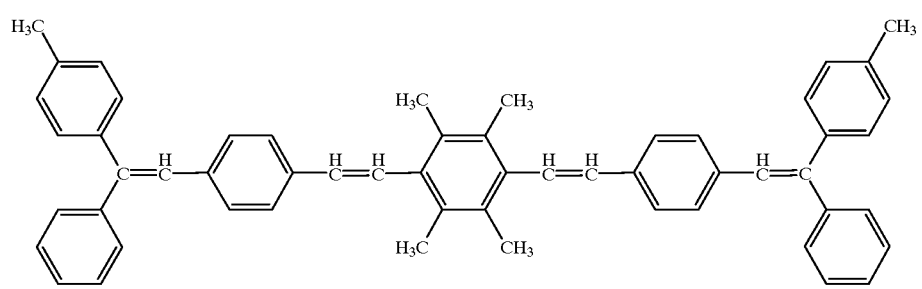

-continued
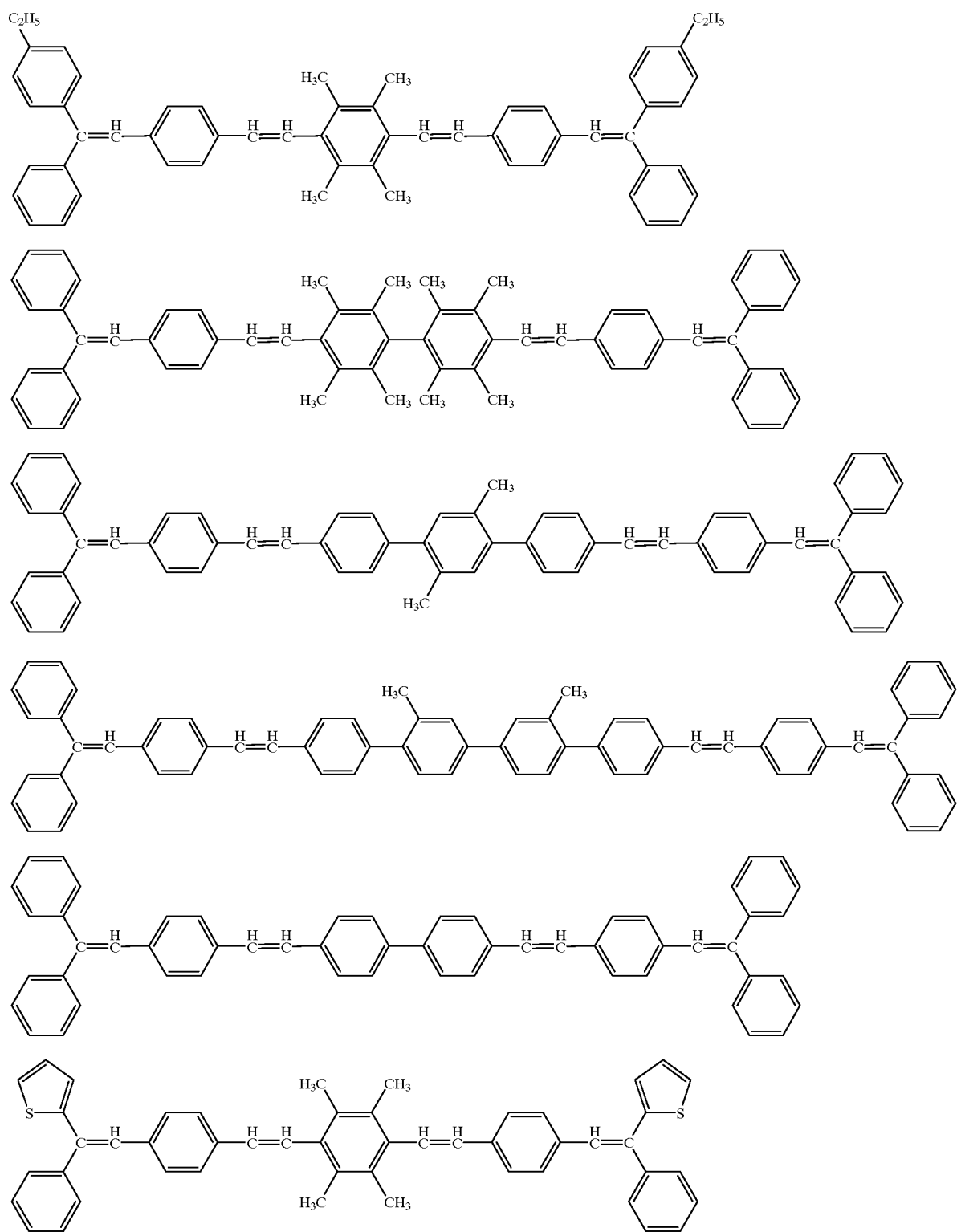

-continued
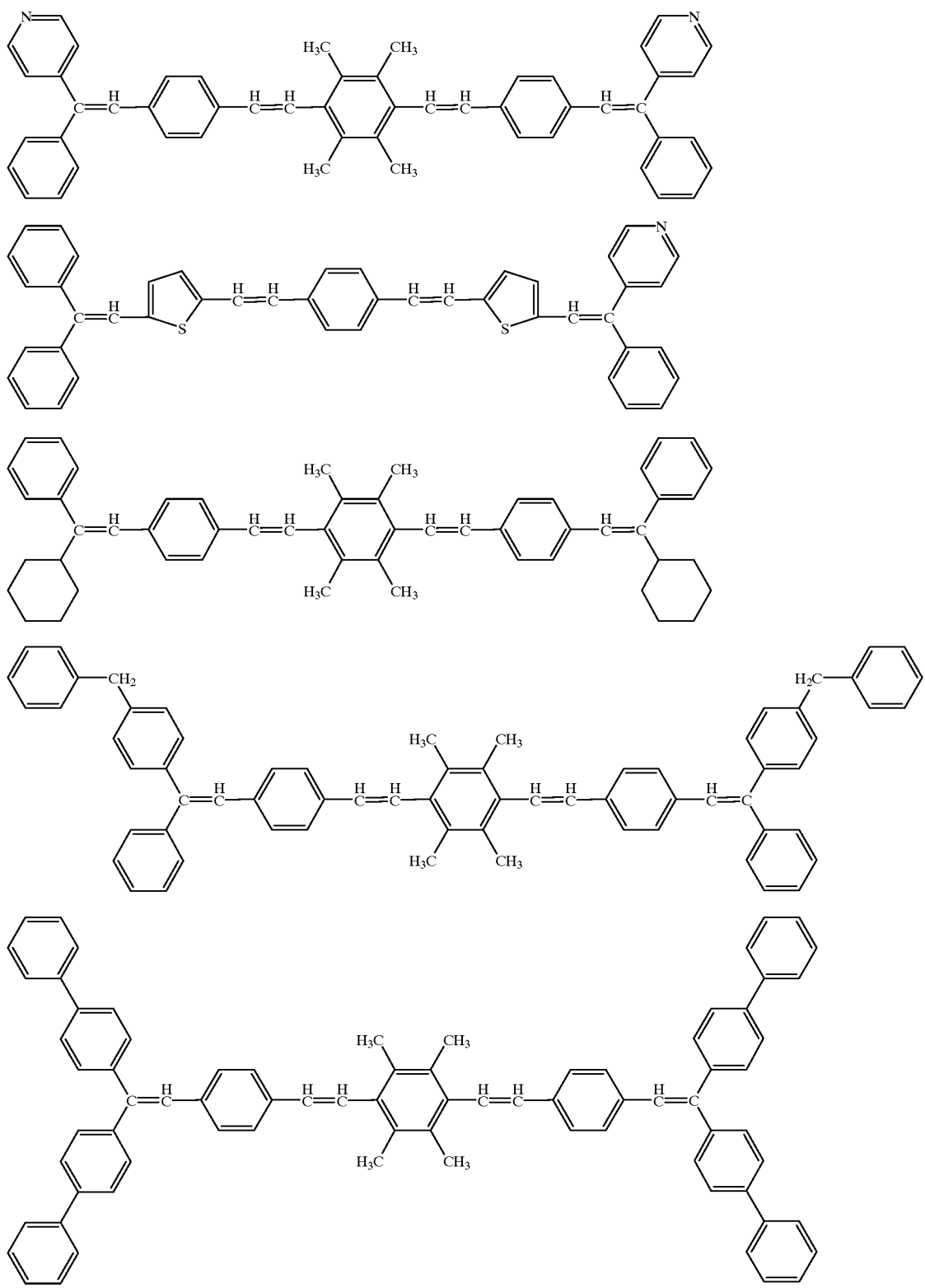

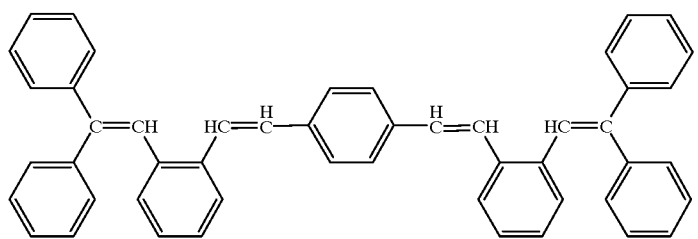
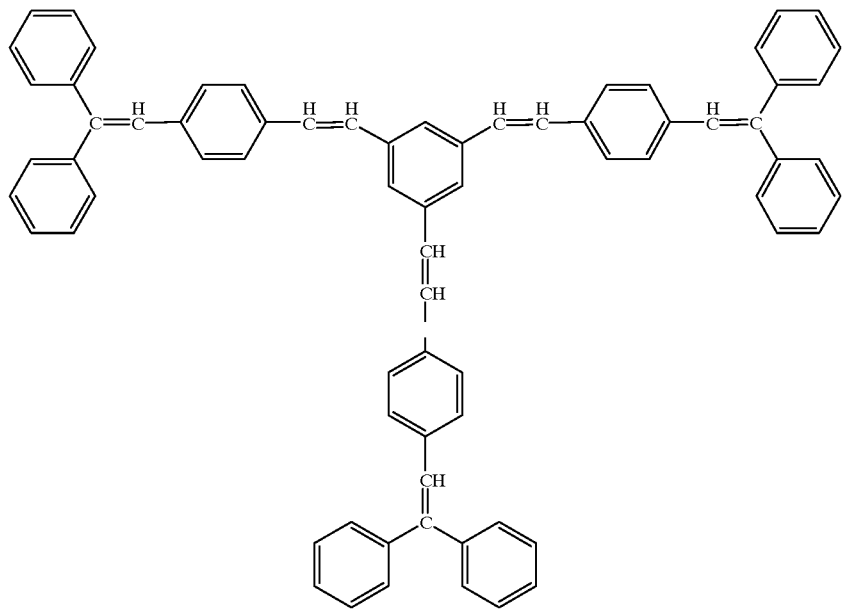
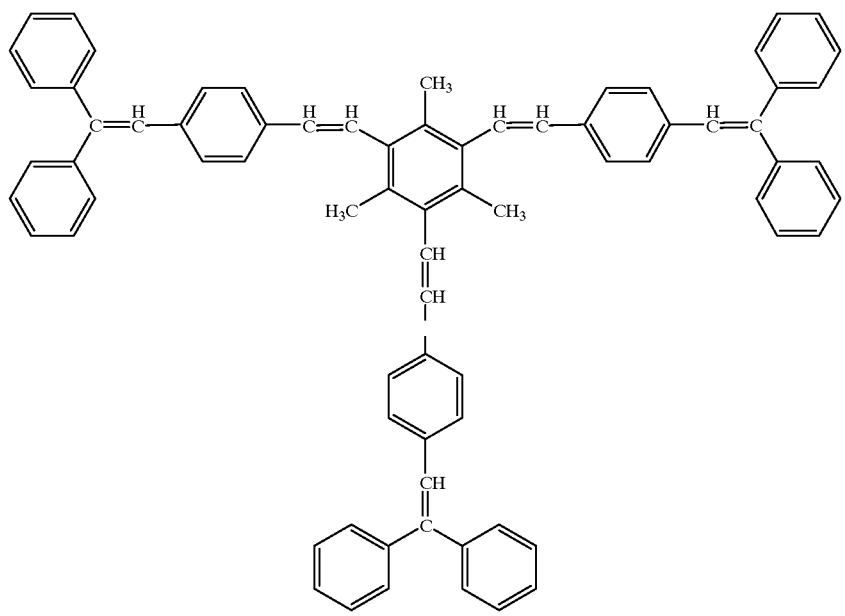

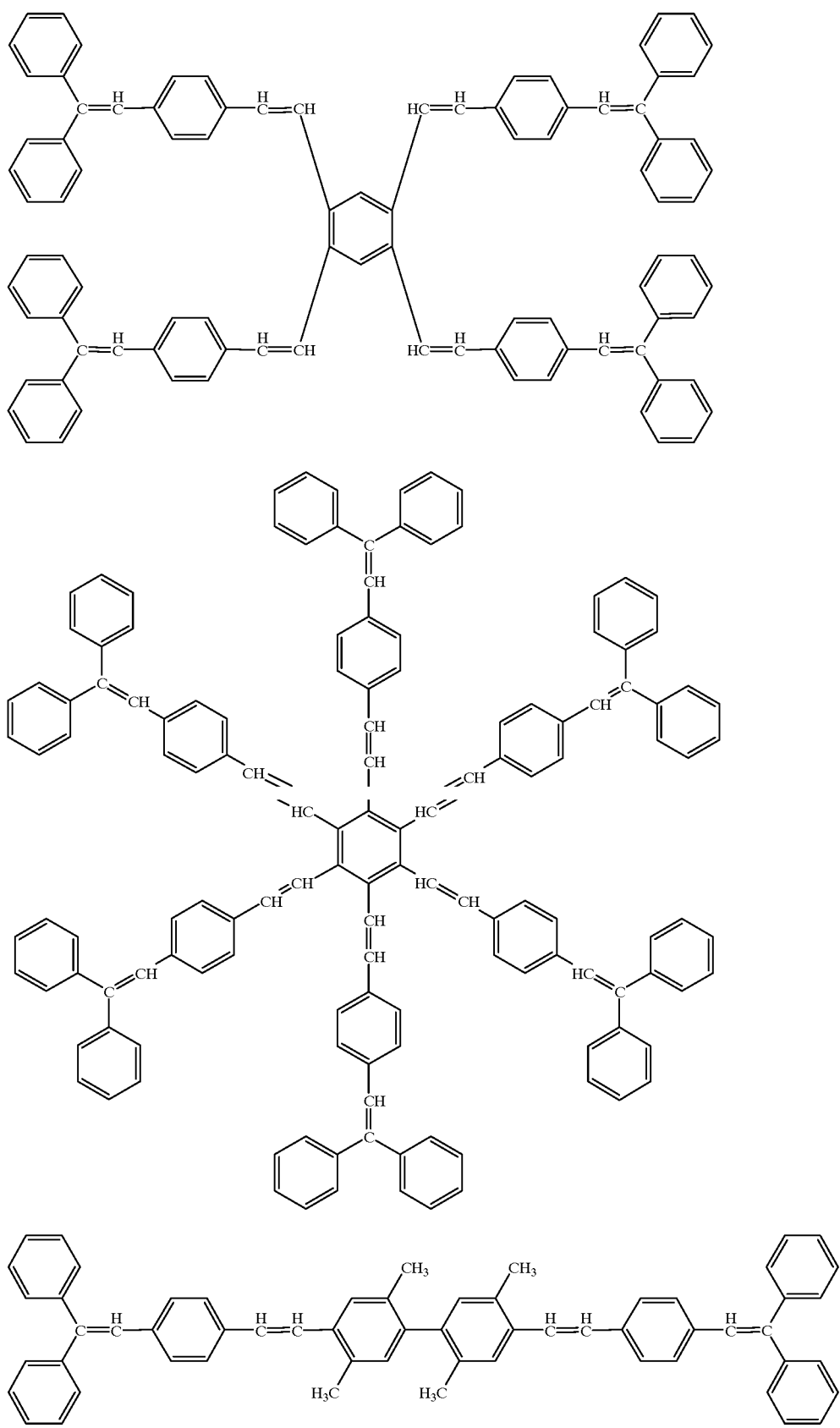

-continued

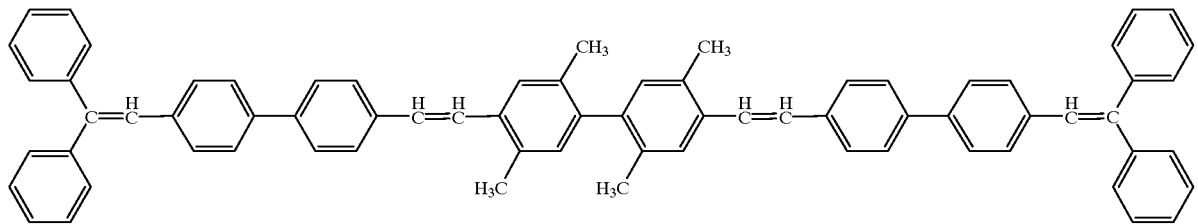

4. An organic electron luminescent device comprising a pair of electrodes and a layer consisting of a methylidene compound of the following general formula (1)

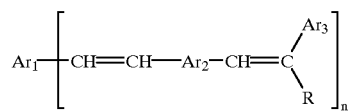

wherein $Ar_1$ represents a substituted or unsubstituted aromatic hydrocarbon residue having 2 to 6 valences, $Ar_2$ represents a divalent substituted or unsubstituted aromatic hydrocarbon residue, $Ar_3$ represents a substituted or unsubstituted aromatic hydrocarbon residue or a substituted or unsubstituted aromatic heterocyclic hydrocarbon residue, R represents a substituted or unsubstituted aromatic hydrocarbon residue, a substituted or unsubstituted aromatic heterocyclic hydrocarbon residue, a substituted or unsubstituted alkyl group provided that $Ar_3$ and R may join to form a ring, and n is an integer of 2 to 6.

* * * * *